United States Patent
Zhang et al.

(10) Patent No.: US 12,383,177 B2
(45) Date of Patent: Aug. 12, 2025

(54) FATIGUE DETECTION IN EXTENDED REALITY APPLICATIONS

(71) Applicant: QUALCOMM Incorporated, San Diego, CA (US)

(72) Inventors: Danlu Zhang, San Diego, CA (US); Parthiban Ellappan, Virudhunagar (IN); Brian Momeyer, Escondido, CA (US); Jiaying Pan, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 71 days.

(21) Appl. No.: 18/066,968

(22) Filed: Dec. 15, 2022

(65) Prior Publication Data

US 2024/0197217 A1 Jun. 20, 2024

(51) Int. Cl.
| | | |
|---|---|---|
| *A61B 5/16* | (2006.01) | |
| *A61B 5/02* | (2006.01) | |
| *G06F 3/01* | (2006.01) | |
| *G06T 17/00* | (2006.01) | |
| *G06V 40/20* | (2022.01) | |

(52) U.S. Cl.
CPC ............. *A61B 5/163* (2017.08); *A61B 5/02* (2013.01); *G06F 3/013* (2013.01); *G06T 17/00* (2013.01); *G06V 40/20* (2022.01)

(58) Field of Classification Search
CPC ........... A61B 5/163; A61B 5/02; G06F 3/013; G06T 17/00; G06V 40/20
USPC .......................................................... 348/77
See application file for complete search history.

(56) References Cited

U.S. PATENT DOCUMENTS

| | | | | |
|---|---|---|---|---|
| 7,769,435 B2* | 8/2010 | Kuo ..................... | A61B 5/6815 | 600/509 |
| 9,579,060 B1* | 2/2017 | Lisy ..................... | A61B 5/4803 | |
| 2003/0028117 A1* | 2/2003 | Hampton ............. | A61B 5/0006 | 600/509 |
| 2011/0270048 A1* | 11/2011 | Addison ............ | A61B 5/14551 | 600/301 |
| 2013/0012790 A1* | 1/2013 | Horseman ............ | A61B 5/6891 | 600/301 |

(Continued)

FOREIGN PATENT DOCUMENTS

| | | |
|---|---|---|
| EP | 3200552 A1 | 8/2017 |
| WO | 2022212052 A1 | 10/2022 |

OTHER PUBLICATIONS

Partial International Search Report—PCT/US2023/078451—ISA/EPO—Feb. 19, 2024.

(Continued)

*Primary Examiner* — Tung T Vo
(74) *Attorney, Agent, or Firm* — Polsinelli/Qualcomm

(57) ABSTRACT

System and techniques are described herein for providing variable rate touch sampling for touch sensors. In one illustrative example, a method of monitoring activity of a person includes obtaining one or more images of a user performing a first movement during a usage instance of an extended reality (XR) device; obtaining first biometric information of the user from at least one first biometric sensor of the XR device while the user performs the first movement; determining fatigue information of the user at least in part based on the one or more images and the first biometric information of the user; and determining an action based on the fatigue information.

36 Claims, 10 Drawing Sheets

(56) References Cited

U.S. PATENT DOCUMENTS

| | | | | |
|---|---|---|---|---|
| 2014/0364212 | A1* | 12/2014 | Osman | A63F 13/537 463/31 |
| 2015/0288944 | A1* | 10/2015 | Nistico | G06F 3/0487 345/156 |
| 2016/0077547 | A1 | 3/2016 | Aimone et al. | |
| 2016/0086500 | A1* | 3/2016 | Kaleal, III | G06Q 10/10 434/257 |
| 2017/0007165 | A1* | 1/2017 | Jain | A61B 5/165 |
| 2017/0039045 | A1* | 2/2017 | Abrahami | A61B 5/486 |
| 2017/0255262 | A1* | 9/2017 | Liu | G06F 3/015 |
| 2018/0001198 | A1* | 1/2018 | Frappiea | A63F 13/2145 |
| 2018/0004478 | A1* | 1/2018 | Chen | A63F 13/26 |
| 2018/0011971 | A1* | 1/2018 | Yeh | G16H 50/30 |
| 2018/0020937 | A1* | 1/2018 | Chou | A61B 5/291 600/301 |
| 2019/0223745 | A1* | 7/2019 | Lee | A61B 5/372 |
| 2019/0223747 | A1* | 7/2019 | Chou | A61B 5/291 |
| 2019/0286232 | A1* | 9/2019 | De Nardi | G06F 3/017 |
| 2020/0027568 | A1* | 1/2020 | Foshee, Jr. | A61B 1/227 |
| 2020/0113472 | A1* | 4/2020 | Mandel-Portnoy | G16H 10/60 |
| 2020/0163563 | A1* | 5/2020 | Meyer | A61B 5/318 |
| 2020/0285310 | A1* | 9/2020 | Sazuka | G02B 27/0093 |
| 2020/0294652 | A1* | 9/2020 | Burdea | A61B 5/4848 |
| 2021/0045647 | A1* | 2/2021 | Barnacka | A61B 5/7246 |
| 2021/0169417 | A1* | 6/2021 | Burton | A61B 5/4857 |
| 2021/0282639 | A1* | 9/2021 | Yokoyama | G02B 27/02 |
| 2021/0381806 | A1* | 12/2021 | Colachis | A61N 1/0456 |
| 2022/0125323 | A1* | 4/2022 | Smith | A61B 5/1102 |
| 2022/0134048 | A1* | 5/2022 | Gruneberg | A61N 7/00 600/28 |
| 2022/0280105 | A1* | 9/2022 | Dixit | A61B 5/02405 |
| 2022/0384027 | A1* | 12/2022 | Kaleal, III | A61B 5/11 |
| 2023/0144578 | A1* | 5/2023 | Castleman | G06F 3/011 345/8 |
| 2023/0329636 | A1* | 10/2023 | Ramp | G16H 40/63 |
| 2024/0139463 | A1* | 5/2024 | Lal | A61M 21/00 |
| 2024/0197217 | A1* | 6/2024 | Zhang | G06T 17/00 |
| 2024/0245352 | A1* | 7/2024 | Korkala | A61B 5/6823 |

OTHER PUBLICATIONS

International Search Report and Written Opinion—PCT/US2023/078451—ISA/EPO—May 10, 2024.

* cited by examiner

FATIGUE DETECTION IN EXTENDED REALITY APPLICATIONS

FIELD

The present disclosure generally relates to fatigue detection in extended reality (XR) applications. In some examples, aspects of the present disclosure are related to providing a directed movement application in an XR device and detecting fatigue of the user of the XR device.

BACKGROUND

Extended reality technologies can be used to present virtual content to users, and/or can combine real environments from the physical world and virtual environments to provide users with extended reality (XR) experiences. The term XR can encompass virtual reality (VR), augmented reality (AR), mixed reality, and the like. Extended reality systems can allow users to experience XR environments by overlaying virtual content onto images of a real-world environment, which can be viewed by a user through an XR device (e.g., a head-mounted display, extended reality glasses, or other devices). An XR device is a device that displays an environment to a user, for example through a head-mounted display (HMD) or other device. The environment is at least partially different from the real-world environment in which the user is in. The user can generally change their view of the environment interactively, for example by tilting or moving the HMD or other device.

In some cases, an XR device can include a "see-through" display that allows the user to see their real-world environment based on light from the real-world environment passing through the display. In some cases, an XR device can include a "pass-through" display that allows the user to see their real-world environment, or a virtual environment based on their real-world environment, based on a view of the environment being captured by one or more cameras and displayed on the display. "See-through" or "pass-through" XR devices can be worn by users while the users are engaged in activities in their real-world environment.

While the goal of many XR devices is to create realistic, interactive, and fully immersive XR environments, XR devices should also ensure that virtual content does not create potentially dangerous situations for users, or otherwise prevent users from properly interacting with the real-world environment. Improved XR devices are needed to dynamically adapt virtual content based on features of the real-world environment.

SUMMARY

In some examples, systems and techniques are described for detecting fatigue in extended reality (XR) applications. The systems and techniques can improve engagement and safety of different types of XR applications.

According to at least one example, a method is provided for monitoring activity of a person. The method includes: obtaining one or more images of a user performing a first movement during a usage instance of an XR device; obtaining first biometric information of the user from at least one first biometric sensor of the XR device while the user performs the first movement; determining fatigue information of the user at least in part based on the one or more images and the first biometric information of the user; and determining an action based on the fatigue information.

In another example, an apparatus for monitoring activity of a person is provided that includes at least one memory and at least one processor coupled to the at least one memory. The at least one processor is configured to: obtain one or more images of a user performing a first movement during a usage instance of an XR device; obtain first biometric information of the user from at least one first biometric sensor of the XR device while the user performs the first movement; determine fatigue information of the user at least in part based on the one or more images and the first biometric information of the user; and determine an action based on the fatigue information.

In another example, a non-transitory computer-readable medium is provided that has stored thereon instructions that, when executed by one or more processors, cause the one or more processors to: obtain one or more images of a user performing a first movement during a usage instance of an XR device; obtain first biometric information of the user from at least one first biometric sensor of the XR device while the user performs the first movement; determine fatigue information of the user at least in part based on the one or more images and the first biometric information of the user; and determine an action based on the fatigue information.

In another example, an apparatus for monitoring activity of a person is provided. The apparatus includes: means for obtaining one or more images of a user performing a first movement during a usage instance of an XR device; means for obtaining first biometric information of the user from at least one first biometric sensor of the XR device while the user performs the first movement; means for determining fatigue information of the user at least in part based on the one or more images and the first biometric information of the user; and means for determining an action based on the fatigue information.

In some aspects, one or more of the apparatuses described herein is, is part of, and/or includes a mobile device (e.g., a mobile telephone and/or mobile handset and/or so-called "smartphone" or other mobile device), an XR device (e.g., a virtual reality (VR) device, an augmented reality (AR) device, or a mixed reality (MR) device), a head-mounted device (HMD) device, a vehicle or a computing system, device, or component of a vehicle, a wearable device (e.g., a network-connected watch or other wearable device), a wireless communication device, a camera, a personal computer, a laptop computer, a server computer, another device, or a combination thereof. In some aspects, the apparatus includes a camera or multiple cameras for capturing one or more images. In some aspects, the apparatus further includes a display for displaying one or more images, notifications, and/or other displayable data. In some aspects, the apparatuses described above can include one or more sensors (e.g., one or more inertial measurement units (IMUs), such as one or more gyroscopes, one or more gyrometers, one or more accelerometers, any combination thereof, and/or other sensors).

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and aspects, will become more apparent upon referring to the following specification, claims, and accompanying drawings.

BRIEF DESCRIPTION OF THE DRAWINGS

Illustrative aspects of the present application are described in detail below with reference to the following figures.

DETAILED DESCRIPTION

Figure 1:
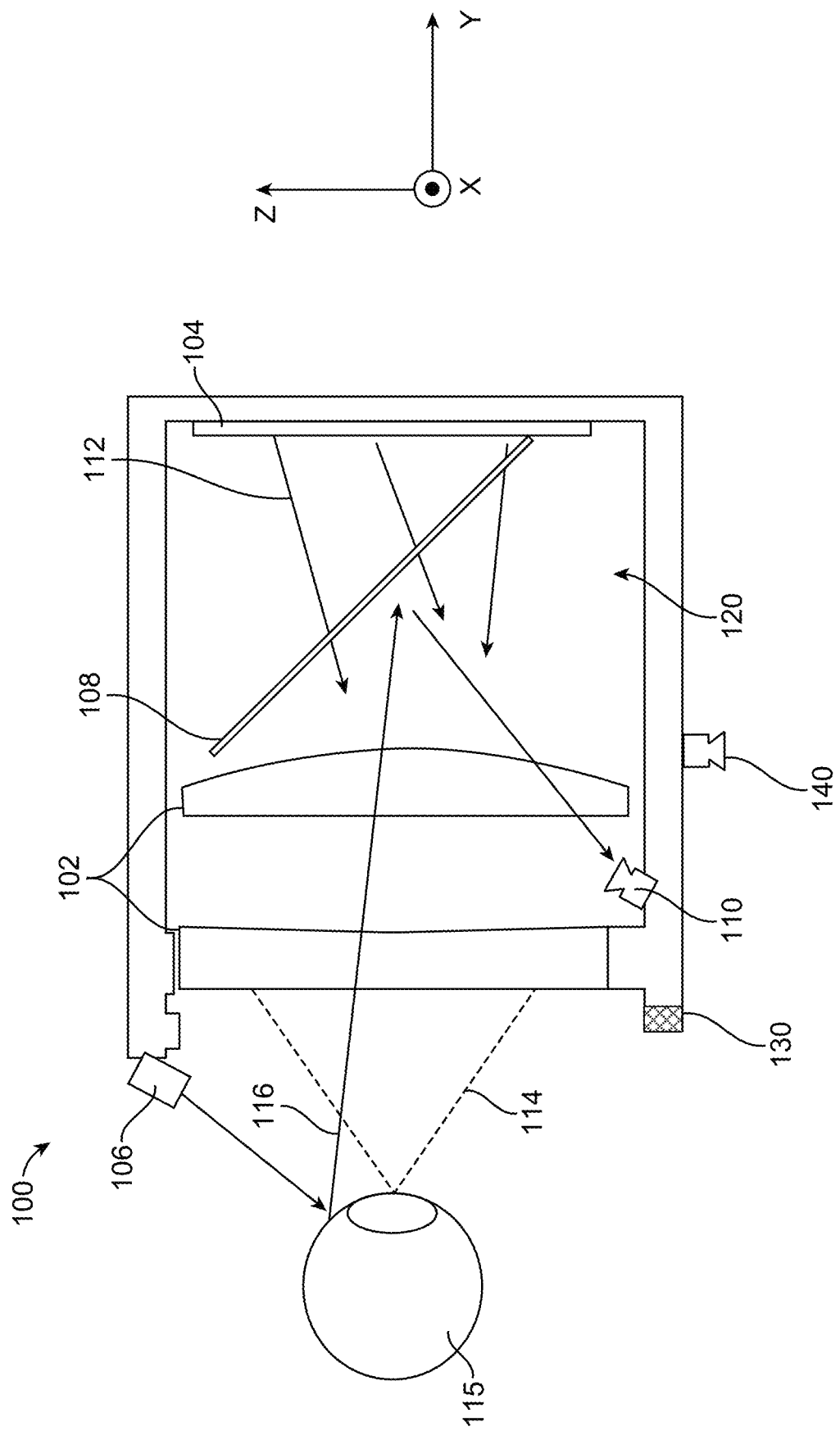
FIG. 1 is a block diagram illustrating a simplified cross-sectional view of a lens assembly of an extended reality system, in accordance with some examples.

Certain aspects of this disclosure are provided below. Some of these aspects may be applied independently and some of them may be applied in combination as would be apparent to those of skill in the art. In the following description, for the purposes of explanation, specific details are set forth in order to provide a thorough understanding of aspects of the application. However, it will be apparent that various aspects may be practiced without these specific details. The figures and descriptions are not intended to be restrictive.

The ensuing description provides example aspects only and is not intended to limit the scope, applicability, or configuration of the disclosure. Rather, the ensuing description of the example aspects will provide those skilled in the art with an enabling description for implementing an example aspect. It should be understood that various changes may be made in the function and arrangement of elements without departing from the spirit and scope of the application as set forth in the appended claims.

The terms "exemplary" and/or "example" are used herein to mean "serving as an example, instance, or illustration." Any aspect described herein as "exemplary" and/or "example" is not necessarily to be construed as preferred or advantageous over other aspects. Likewise, the term "aspects of the disclosure" does not require that all aspects of the disclosure include the discussed feature, advantage or mode of operation.

A camera is a device that receives light and captures image frames, such as still images or video frames, using an image sensor. The terms "image," "image frame," and "frame" are used interchangeably herein. Cameras can be configured with a variety of image capture and image processing settings. The different settings result in images with different appearances. Some camera settings are determined and applied before or during capture of one or more image frames, such as ISO, exposure time, aperture size, f/stop, shutter speed, focus, and gain. For example, settings or parameters can be applied to an image sensor for capturing the one or more image frames. Other camera settings can configure post-processing of one or more image frames, such as alterations to contrast, brightness, saturation, sharpness, levels, curves, or colors. For example, settings or parameters can be applied to a processor (e.g., an image signal processor or ISP) for processing the one or more image frames captured by the image sensor.

Extended reality (XR) systems or devices can provide virtual content to a user and/or can combine real-world or physical environments and virtual environments (made up of virtual content) to provide users with XR experiences. The real-world environment can include real-world objects (also referred to as physical objects), such as people, vehicles, buildings, tables, chairs, and/or other real-world or physical objects. XR systems or devices can facilitate interaction with different types of XR environments (e.g., a user can use an XR system or device to interact with an XR environment). XR devices can include virtual reality (VR) systems facilitating interactions with VR environments, augmented reality (AR) systems facilitating interactions with AR environments, mixed reality (MR) systems facilitating interactions with MR environments, and/or other XR devices. Examples of XR systems or devices include head-mounted displays (HMDs), smart glasses, among others. In some cases, an XR device can track parts of the user (e.g., a hand and/or fingertips of a user) to allow the user to interact with items of virtual content.

In some cases, an XR device can include an optical "see-through" or "pass-through" display (e.g., see-through or pass-through AR HMD or AR glasses), allowing the XR device to display XR content (e.g., AR content) directly onto a real-world view without displaying video content. For example, a user may view physical objects through a display (e.g., glasses or lenses), and the AR system can display AR content onto the display to provide the user with an enhanced visual perception of one or more real-world objects. In one example, a display of an optical see-through AR system can include a lens or glass in front of each eye (or a single lens or glass over both eyes). The see-through display can allow the user to see a real-world or physical object directly, and can display (e.g., projected or otherwise displayed) an enhanced image of that object or additional AR content to augment the user's visual perception of the real world.

An XR device can include one or more user-facing sensors that face the user, such as user-facing image sensors (or cameras) that face the user. For instance, the user-facing sensors can face the user's face, eyes, one or more other portions of the user's body, and/or a combination thereof.

In some cases, the immersive nature of XR devices can be used for interactive applications that encourage human movement. For example, a user may be interacting with an XR environment in which the user may physically exert themselves and become fatigued. While the goal of many XR devices or systems is to create realistic, interactive, and fully immersive XR environments, XR devices should also prevent virtual content from exhausting or otherwise affecting the user. In some cases, user fatigue can cause adverse effects, such as inadvertently causing the user to fall from fatigue.

The present disclosure describes systems, apparatuses, methods, and computer-readable media (collectively referred to as "systems and techniques") for monitoring user activity information to detect fatigue of a user of an XR device within an XR environment. For example, a system can obtain one or more images of a user performing a first movement during a usage instance of an XR device, such as during virtual session of the XR device where the XR device is outputting virtual content, during usage of an application of the XR device, etc. The system can obtain biometric information of the user from at least one biometric sensor of the XR device while the user performs the first movement. The system can determine fatigue information of the user based on the one or more images and the first biometric information of the user and can determine a corrective action based on the fatigue information.

In some cases, the user activity information can include physiological information of the user (e.g., the biometric information), such as a heart rate and/or blood pressure, that can indicate that the user is fatigued. For example, the systems and techniques can monitor the user's heart rate (e.g., to detect irregular heartbeats). Based on the heart rate and/or other user activity information, the systems and techniques can determine that the user Is fatigued. Other aspects include determining that a user of an XR device or system has low interest in the XR environment, which can be a factor in identifying fatigue. For example, eyes of a user tend to move to focus on areas that are of interest to the user. By comparing areas (e.g., in an image) of the XR environment for which the eyes of the user are focused to areas of the XR environment that are determined to be of potential interest to the user (e.g., a region of interest (ROI)), the XR device or system can determine an extent of the user's attention with respect to the XR environment.

In some cases, the XR device can be configured to adapt a virtual application based on user activity information. As noted above, in some aspects, the user activity information includes physiological information (e.g., heart rate, blood pressure, temperature, etc.) and motion information. As an example, the XR device may determine that the user's heart rate is indicative of fatigue and may modify the virtual application to reduce the user's heart rate. In one aspect, the XR device can cause the user to engage in a resting position, to perform controlled breathing to reduce various physiological effects (e.g., reduce the heart rate). In other cases, the XR device can configure a different exercise with lower intensity. The quality of the motion can also be measured to determine if a muscle or a muscle group is fatigued, and the XR device can adapt the movement the user is to provide to allow that muscle or muscle group to recover. For example, in an XR boxing game, the XR device can identify that a right arm is fatigued based on a slow speed of motion input on a particular arm. In that case, the XR device can switch movement to be primarily focused on the opposing arm that is not fatigued.

In some aspects, the motion quality can be based on a number of parameters, such as the path of movement, time of the movement, and so forth. For example, if the duration of the movement is longer than a threshold (e.g., if a pushup takes longer than 4 seconds), the system can determine that the user is fatigued. In some aspects, fatigue can be identified based on motion from a path associated with a movement. For example, a squat is ideally a straight vertical movement along a vertical line and exhaustion can be identified based on the amount of motion that deviates from the vertical line. In the case of an XR boxing game, the hand motion may traverse downward during the movements.

In one aspect, the XR device can cause the user to disengage from the usage instance by disabling the XR application for a period of time. In some cases, the XR device can be configured to allow the user to reengage based on passing one or more physiological measurements that are indicative of the user being rested. For example, the heart rate may recover in a short period of time, but blood pressure has a longer recovery period. In this case, the XR device can be configured to allow the user to reengage based on a heart rate and blood pressure being lower than a particular threshold. In some cases, weights (e.g., non-linear weights) can be applied to the physiological measurements. For example, a higher weight can be applied to the blood pressure as compared to a weight applied to the heart rate. In another example, if the heart rate of the user is below 100 pulses per minute (PPM), the heart rate may have an equal weight as blood pressure, and if the heart rate of the user is below 100 PPM, the heart rate has less weight as compared to blood pressure.

Additional details and aspects of the present disclosure are described in more detail below with respect to the figures.

Various aspects of the techniques described herein will be discussed below with respect to the figures. FIG. 1 is a diagram illustrating a simplified cross-sectional view of lens assembly 100 (e.g., of an HMD). In the illustrated example of FIG. 1, the lens assembly 100 includes a lens system 102, a display 104, an illumination source 106, a light directing component 108, and an image sensor 110.

As illustrated, light from the display 104 can pass through the light directing component 108 and be focused by the lens system 102 on the user's eye 115. In some implementations, the light directing component 108 can be configured to allow visible light from the display 104 to pass through. In the illustrated example of FIG. 1, the light directing component 108 is positioned within a cavity 120 of the lens assembly 100 between the lens system 102 and the display 104. As illustrated in FIG. 1, the visible light 112 can be focused at the position of the user's eye 115 as illustrated by lines 114. In some cases, the light directing component 108 can be configured to reflect other wavelengths of light, such as infrared (IR) light. In some examples, the light directing component 108 can be implemented using a reflective coating. In some implementations, the light directing component 108 can include a dielectric material that passes visible light and reflects IR light. In some examples, the light directing component can be coated with a transparent conductor. In one illustrative example, an indium-tin-oxide (ITO) material that is transparent to visible light and reflects IR light can be used to coat the light directing component 108. The illumination source 106 can be an IR illumination source (e.g., an IR light emitting diode (LED)) that illuminates the user's eye 115. When the IR light reaches the user's eye, a scattered and/or reflected portion of the light, such as the example ray 116 can reach the light directing component 108 and reflect toward the image sensor 110.

The image sensor 110 can be an IR image sensor that can detect the scattered and/or reflected light from the eye to form one or more images. In some cases, an XR device can obtain image data from the image sensor 110 and track the user's eye position and/or gaze direction based on the obtained data.

In some cases, the position of a user's eyes relative to the lens assembly 100 can vary. For example, each individual user may have different eyes size, face shape, face symmetry, eye separation, facial feature alignment, and/or a combination thereof. In some implementations, an eye tracking system can be configured to perform eye tracking over a specified range of eye positions and/or rotations using the image data collected, for example, from the image sensor 110. In some cases, if the user's eye moves outside of the specific range, the XR device may be unable to perform eye tracking until the eye returns to a position and/or rotation within the specific range. For example, if the user's eye 115 shown in FIG. 1 rotates to look down (e.g., toward the negative z-axis direction), the image of the user's eye 115 may be obstructed by eyelashes and/or by the curvature of the user's eye 115. In some cases, the range of eye tracking may be limited by the desire to keep the lens assembly of an XR device compact.

In some cases, the systems and techniques described herein can be used to obtain eye tracking data across the complete range of motion (e.g., translation and/or rotation) of a user's eye. In some cases, the systems and techniques described herein can be used to obtain eye tracking data over a wider range of eye position and/or rotation achievable by a single eye tracking system. By utilizing two or more eye trackers with light directing components (e.g., light directing component 108 of FIG. 1) oriented along different axes (e.g., vertical and horizontal), the overall field of view of eye tracking systems can be extended to include the combined eye tracking field of view of all of the two or more sensors. In some cases, each eye tracking system may have a wider field of view for motion and/or rotation along a first axis (e.g., the axis of orientation of the light directing component) and a narrower field of view along a second axis, perpendicular to the first axis. In some cases, the distance of the displayed image (e.g., a projected virtual image) from a display can be far enough away from a user's eyes that the user's eyes will move together when looking at the display. In some cases, an eye tracker oriented in the first direction can track position and/or rotation of a first eye of a user, and an eye tracker oriented in the second direction can track the position and/or rotation of the second eye of a user. In some implementations, the overall range for eye tracking can be increased using eye tracking on the data from both eye trackers. For example, one eye tracker can be used to track vertical movement and/or rotation of the first eye, and another eye tracker can be used to track horizontal movement and/or rotation of the second eye. Because the eyes move together, as long as one of the eyes is within range of either of the eye trackers, the position of both of the user's eyes can be determined.

The lens assembly 100 also includes a photoplethysmography (PPG) sensor 130 that is disposed at a surface of the lens assembly 100 and configured to detect biometric information. In one aspect, the PPG sensor 130 is configured to measure blood below the surface of a user's skin that can be converted into physiological information. For example, the PPG sensor 130 may be used to measure heart rate, blood pressure, and other properties of the blood. The PPG sensor 130 can be disposed on the lens assembly 100 at various points of the lens assembly 100 such as a lateral edge of the lens assembly 100 that is proximate to the temple. In other aspects, the PPG sensor 130 can be disposed on any suitable location on the lens assembly 100.

In other aspects, the lens assembly 100 may also include a vertically oriented image sensor 140. In the illustrated example, the image sensor 140 is configured to point downwards to capture images related to respiratory functions of the user. For example, the lens assembly 100 may measure a respiratory rate (e.g., the breathing rate of the user) based on the image sensor 140 being oriented towards the nose of the user, the mouth of the user, and/or the chest of the user. Other types of sensors can be implemented to detect respiratory rate, such as radio frequency (RF) sensing. In some aspects, high frequency (e.g., 60 GHZ) RF may be used to measure distance based on phase differences.

While examples are described herein for eye tracking in XR devices, the eye tracking systems and techniques described herein can be used for eye tracking with other types of devices and with other geometries. Of note, the illustration in FIG. 1 is not to scale and is provided only for the purposes of illustration. In addition, more or fewer components can be included in the lens assembly 100 of FIG. 1 without departing from the scope of the present disclosure.

Figure 2:
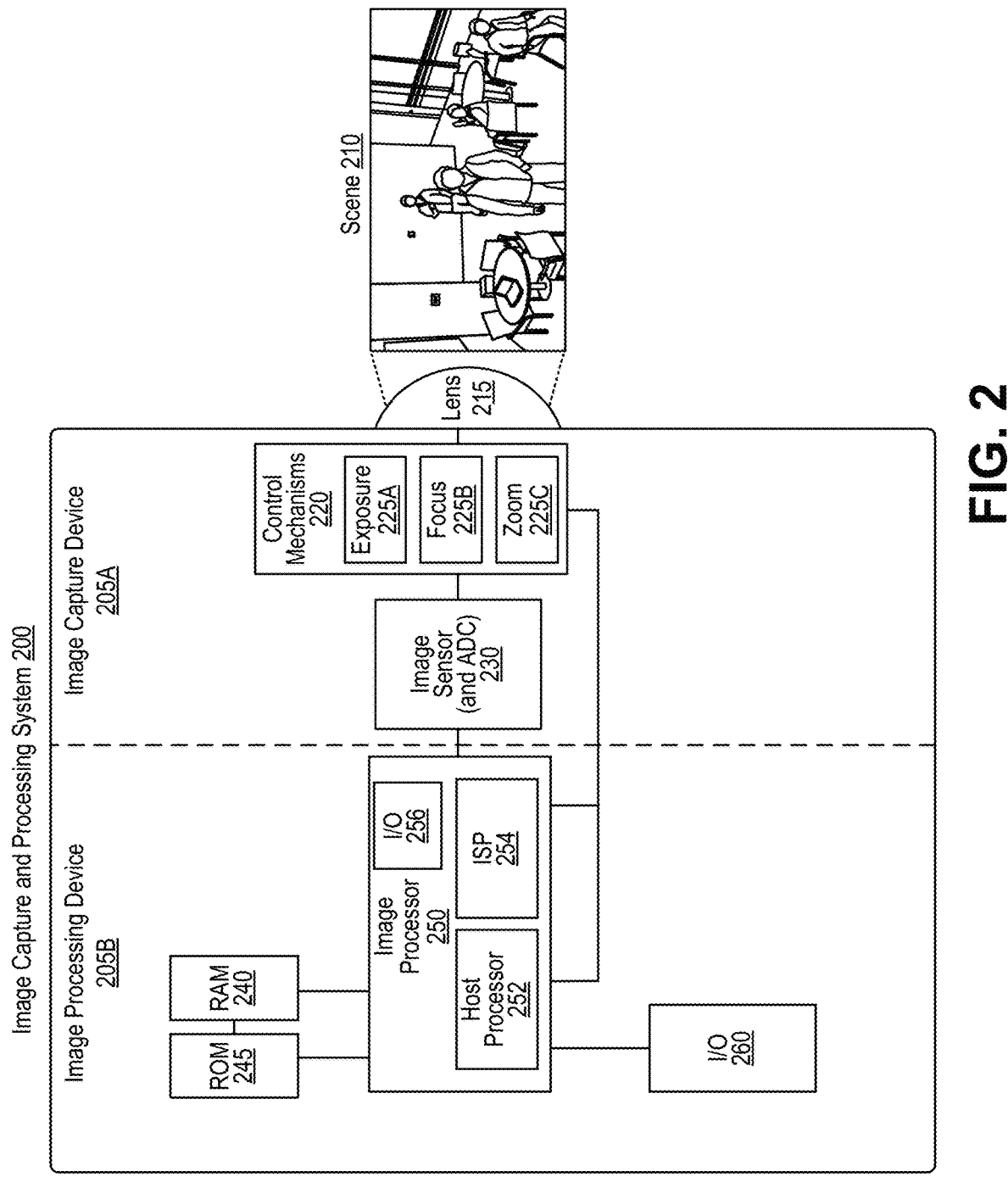
FIG. 2 is a block diagram illustrating an architecture of an image capture and processing system, in accordance with some examples.

FIG. 2 is a block diagram illustrating an architecture of an image capture and processing system 200. The image capture and processing system 200 includes various components that are used to capture and process images of scenes (e.g., an image of a scene 210). The image capture and processing system 200 can capture standalone images (or photographs) and/or can capture videos that include multiple images (or video frames) in a particular sequence. In some cases, the lens 215 and image sensor 230 can be associated with an optical axis. In one illustrative example, the photosensitive area of the image sensor 230 (e.g., the photodiodes) and the lens 215 can both be centered on the optical axis. A lens 215 of the image capture and processing system 200 faces a scene 210 and receives light from the scene 210. The lens 215 bends incoming light from the scene toward the image sensor 230. The light received by the lens 215 passes through an aperture. In some cases, the aperture (e.g., the aperture size) is controlled by one or more control mechanisms 220 and is received by an image sensor 230. In some cases, the aperture can have a fixed size.

The one or more control mechanisms 220 may control exposure, focus, and/or zoom based on information from the image sensor 230 and/or based on information from the image processor 250. The one or more control mechanisms 220 may include multiple mechanisms and components; for instance, the control mechanisms 220 may include one or more exposure control mechanisms 225A, one or more focus control mechanisms 225B, and/or one or more zoom control mechanisms 225C. The one or more control mechanisms 220 may also include additional control mechanisms besides those that are illustrated, such as control mechanisms controlling analog gain, flash, HDR, depth of field, and/or other image capture properties.

The focus control mechanism 225B of the control mechanisms 220 can obtain a focus setting. In some examples, focus control mechanism 225B stores the focus setting in a memory register. Based on the focus setting, the focus control mechanism 225B can adjust the position of the lens 215 relative to the position of the image sensor 230. For example, based on the focus setting, the focus control mechanism 225B can move the lens 215 closer to the image sensor 230 or farther from the image sensor 230 by actuating a motor or servo (or other lens mechanism), thereby adjusting focus. In some cases, additional lenses may be included in the image capture and processing system 200, such as one or more microlenses over each photodiode of the image sensor 230, which each bend the light received from the lens 215 toward the corresponding photodiode before the light reaches the photodiode. The focus setting may be determined via contrast detection autofocus (CDAF), phase detection autofocus (PDAF), hybrid autofocus (HAF), or some combination thereof. The focus setting may be determined using the control mechanism 220, the image sensor 230, and/or the image processor 250. The focus setting may be referred to as an image capture setting and/or an image processing setting. In some cases, the lens 215 can be fixed relative to the image sensor and focus control mechanism 225B can be omitted without departing from the scope of the present disclosure.

The exposure control mechanism 225A of the control mechanisms 220 can obtain an exposure setting. In some cases, the exposure control mechanism 225A stores the exposure setting in a memory register. Based on this exposure setting, the exposure control mechanism 225A can control a size of the aperture (e.g., aperture size or f/stop), a duration of time for which the aperture is open (e.g., exposure time or shutter speed), a duration of time for which the sensor collects light (e.g., exposure time or electronic shutter speed), a sensitivity of the image sensor 230 (e.g., ISO speed or film speed), analog gain applied by the image sensor 230, or any combination thereof. The exposure setting may be referred to as an image capture setting and/or an image processing setting.

The zoom control mechanism 225C of the control mechanisms 220 can obtain a zoom setting. In some examples, the zoom control mechanism 225C stores the zoom setting in a memory register. Based on the zoom setting, the zoom control mechanism 225C can control a focal length of an assembly of lens elements (lens assembly) that includes the lens 215 and one or more additional lenses. For example, the zoom control mechanism 225C can control the focal length of the lens assembly by actuating one or more motors or servos (or other lens mechanism) to move one or more of the lenses relative to one another. The zoom setting may be referred to as an image capture setting and/or an image processing setting. In some examples, the lens assembly may include a parfocal zoom lens or a varifocal zoom lens. In some examples, the lens assembly may include a focusing lens (which can be lens 215 in some cases) that receives the light from the scene 210 first, with the light then passing through an afocal zoom system between the focusing lens (e.g., lens 215) and the image sensor 230 before the light reaches the image sensor 230. The afocal zoom system may, in some cases, include two positive (e.g., converging, convex) lenses of equal or similar focal length (e.g., within a threshold difference of one another) with a negative (e.g., diverging, concave) lens between them. In some cases, the zoom control mechanism 225C moves one or more of the lenses in the afocal zoom system, such as the negative lens and one or both of the positive lenses. In some cases, zoom control mechanism 225C can control the zoom by capturing an image from an image sensor of a plurality of image sensors (e.g., including image sensor 230) with a zoom corresponding to the zoom setting. For example, image capture and processing system 200 can include a wide-angle image sensor with a relatively low zoom and a telephoto image sensor with a greater zoom. In some cases, based on the selected zoom setting, the zoom control mechanism 225C can capture images from a corresponding sensor.

The image sensor 230 includes one or more arrays of photodiodes or other photosensitive elements. Each photodiode measures an amount of light that eventually corresponds to a particular pixel in the image produced by the image sensor 230. In some cases, different photodiodes may be covered by different filters. In some cases, different photodiodes can be covered in color filters, and may thus measure light matching the color of the filter covering the photodiode. Various color filter arrays can be used, including a Bayer color filter array, a quad color filter array (also referred to as a quad Bayer color filter array or QCFA), and/or any other color filter array. For instance, Bayer color filters include red color filters, blue color filters, and green color filters, with each pixel of the image generated based on red light data from at least one photodiode covered in a red color filter, blue light data from at least one photodiode covered in a blue color filter, and green light data from at least one photodiode covered in a green color filter.

Returning to FIG. 2, other types of color filters may use yellow, magenta, and/or cyan (also referred to as "emerald") color filters instead of or in addition to red, blue, and/or green color filters. In some cases, photodiodes may be configured to measure IR light. In some implementations, photodiodes measuring IR light may not be covered by any filter, thus allowing IR photodiodes to measure both visible (e.g., color) and IR light. In some examples, IR photodiodes may be covered by an IR filter, allowing IR light to pass through and blocking light from other parts of the frequency spectrum (e.g., visible light, color). Some image sensors (e.g., image sensor 230) may lack filters (e.g., color, IR, or any other part of the light spectrum) altogether and may instead use different photodiodes throughout the pixel array (in some cases vertically stacked). The different photodiodes throughout the pixel array can have different spectral sensitivity curves, therefore responding to different wavelengths of light. Monochrome image sensors may also lack filters and therefore lack color depth.

In some cases, the image sensor 230 may alternately or additionally include opaque and/or reflective masks that block light from reaching certain photodiodes, or portions of certain photodiodes, at certain times and/or from certain angles. In some cases, opaque and/or reflective masks may be used for PDAF. In some cases, the opaque and/or reflective masks may be used to block portions of the electromagnetic spectrum from reaching the photodiodes of the image sensor (e.g., an IR cut filter, an ultraviolet (UV) cut filter, a band-pass filter, low-pass filter, high-pass filter, or the like). The image sensor 230 may also include an analog gain amplifier to amplify the analog signals output by the photodiodes and/or an analog to digital converter (ADC) to convert the analog signals output of the photodiodes (and/or amplified by the analog gain amplifier) into digital signals. In some cases, certain components or functions discussed with respect to one or more of the control mechanisms 220 may be included instead or additionally in the image sensor 230. The image sensor 230 may be a charge-coupled device (CCD) sensor, an electron-multiplying CCD (EMCCD) sensor, an active-pixel sensor (APS), a complimentary metal-oxide semiconductor (CMOS), an N-type metal-oxide semiconductor (NMOS), a hybrid CCD/CMOS sensor (e.g., sCMOS), or some other combination thereof.

Figure 10:
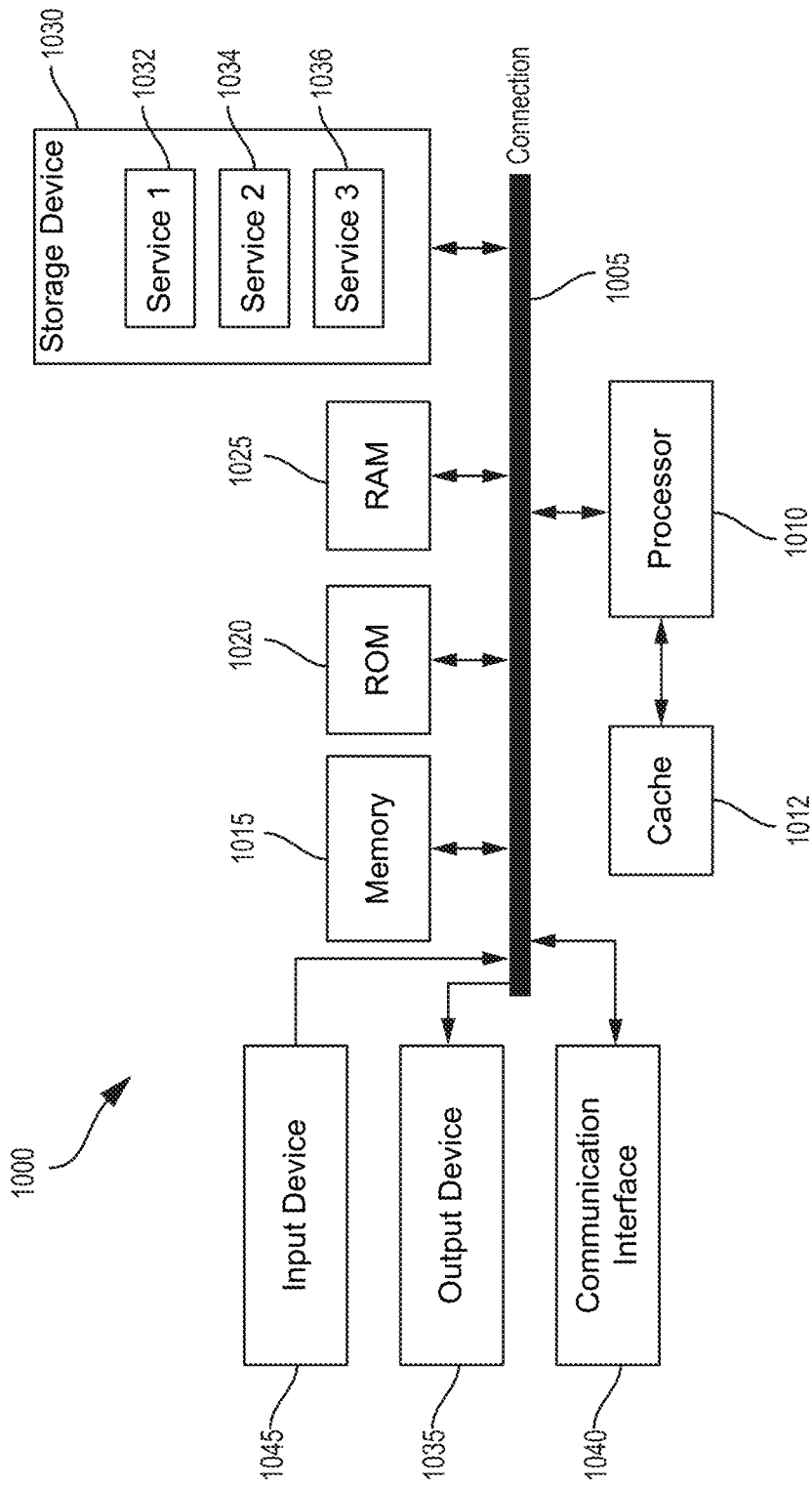
FIG. 10 is a diagram illustrating an example of a system for implementing certain aspects described herein.

The image processor 250 may include one or more processors, such as one or more image signal processors (ISPs) (including ISP 254), one or more host processors (including host processor 252), and/or one or more of any other type of processor 1010 discussed with respect to the computing system 1000 of FIG. 10. The host processor 252 can be a digital signal processor (DSP) and/or other type of processor. In some implementations, the image processor 250 is a single integrated circuit or chip (e.g., referred to as a system-on-chip or SoC) that includes the host processor 252 and the ISP 254. In some cases, the chip can also include one or more input/output ports (e.g., input/output (I/O) ports 256), central processing units (CPUs), graphics processing units (GPUs), broadband modems (e.g., 3G, 4G or LTE, 5G, etc.), memory, connectivity components (e.g., Bluetooth™, Global Positioning System (GPS), etc.), any combination thereof, and/or other components. The I/O ports 256 can include any suitable input/output ports or interface according to one or more protocols or specifications, such as an Inter-Integrated Circuit 2 (I2C) interface, an Inter-Integrated Circuit 3 (I3C) interface, a Serial Peripheral Interface (SPI) interface, a serial General Purpose Input/Output (GPIO) interface, a Mobile Industry Processor Interface (MIPI) (such as a MIPI CSI-2 physical (PHY) layer port or interface, an Advanced High-performance Bus (AHB) bus, any combination thereof, and/or other input/output port. In one illustrative example, the host processor 252 can communicate with the image sensor 230 using an I2C port, and the ISP 254 can communicate with the image sensor 230 using an MIPI port.

The image processor 250 may perform a number of tasks, such as de-mosaicing, color space conversion, image frame downsampling, pixel interpolation, automatic exposure (AE) control, automatic gain control (AGC), CDAF, PDAF, automatic white balance, merging of image frames to form an HDR image, image recognition, object recognition, feature recognition, receipt of inputs, managing outputs, managing memory, or some combination thereof. The image processor 250 may store image frames and/or processed images in random access memory (RAM) 240, read-only memory (ROM) 245, a cache, a memory unit, another storage device, or some combination thereof.

Various input/output (I/O) devices 260 may be connected to the image processor 250. The I/O devices 260 can include a display screen, a keyboard, a keypad, a touchscreen, a trackpad, a touch-sensitive surface, a printer, any other output device, any other input devices, or some combination thereof. In some cases, a caption may be input into the image processing device 205B through a physical keyboard or keypad of the I/O devices 260, or through a virtual keyboard or keypad of a touchscreen of the I/O devices 260. The I/O 260 may include one or more ports, jacks, or other connectors that enable a wired connection between the image capture and processing system 200 and one or more peripheral devices, over which the image capture and processing system 200 may receive data from the one or more peripheral device and/or transmit data to the one or more peripheral devices. The I/O 260 may include one or more wireless transceivers that enable a wireless connection between the image capture and processing system 200 and one or more peripheral devices, over which the image capture and processing system 200 may receive data from the one or more peripheral device and/or transmit data to the one or more peripheral devices. The peripheral devices may include any of the previously-discussed types of I/O devices 260 and may themselves be considered I/O devices 260 once they are coupled to the ports, jacks, wireless transceivers, or other wired and/or wireless connectors.

In some cases, the image capture and processing system 200 may be a single device. In some cases, the image capture and processing system 200 may be two or more separate devices, including an image capture device 205A (e.g., a camera) and an image processing device 205B (e.g., a computing device coupled to the camera). In some implementations, the image capture device 205A and the image processing device 205B may be coupled together, for example via one or more wires, cables, or other electrical connectors, and/or wirelessly via one or more wireless transceivers. In some implementations, the image capture device 205A and the image processing device 205B may be disconnected from one another.

As shown in FIG. 2, a vertical dashed line divides the image capture and processing system 200 of FIG. 2 into two portions that represent the image capture device 205A and the image processing device 205B, respectively. The image capture device 205A includes the lens 215, control mechanisms 220, and the image sensor 230. The image processing device 205B includes the image processor 250 (including the ISP 254 and the host processor 252), the RAM 240, the ROM 245, and the I/O 260. In some cases, certain components illustrated in the image capture device 205A, such as the ISP 254 and/or the host processor 252, may be included in the image capture device 205A.

The image capture and processing system 200 can include an electronic device, such as a mobile or stationary telephone handset (e.g., smartphone, cellular telephone, or the like), a desktop computer, a laptop or notebook computer, a tablet computer, a set-top box, a television, a camera, a display device, a digital media player, a video gaming console, a video streaming device, an Internet Protocol (IP) camera, or any other suitable electronic device. In some examples, the image capture and processing system 200 can include one or more wireless transceivers for wireless communications, such as cellular network communications, 802.11 wi-fi communications, wireless local area network (WLAN) communications, or some combination thereof. In some implementations, the image capture device 205A and the image processing device 205B can be different devices. For instance, the image capture device 205A can include a camera device, and the image processing device 205B can include a computing device, such as a mobile handset, a desktop computer, or other computing device.

While the image capture and processing system 200 is shown to include certain components, one of ordinary skill will appreciate that the image capture and processing system 200 can include more components than those shown in FIG. 2. The components of the image capture and processing system 200 can include software, hardware, or one or more combinations of software and hardware. For example, in some implementations, the components of the image capture and processing system 200 can include and/or can be implemented using electronic circuits or other electronic hardware, which can include one or more programmable electronic circuits (e.g., microprocessors, GPUs, DSPs, CPUs, and/or other suitable electronic circuits), and/or can include and/or be implemented using computer software, firmware, or any combination thereof, to perform the various operations described herein. The software and/or firmware can include one or more instructions stored on a computer-readable storage medium and executable by one or more processors of the electronic device implementing the image capture and processing system 200.

In some examples, the XR device 300 of FIG. 3 (described below) can include the image capture and processing system 200, the image capture device 205A, the image processing device 205B, or a combination thereof.

Figure 3:
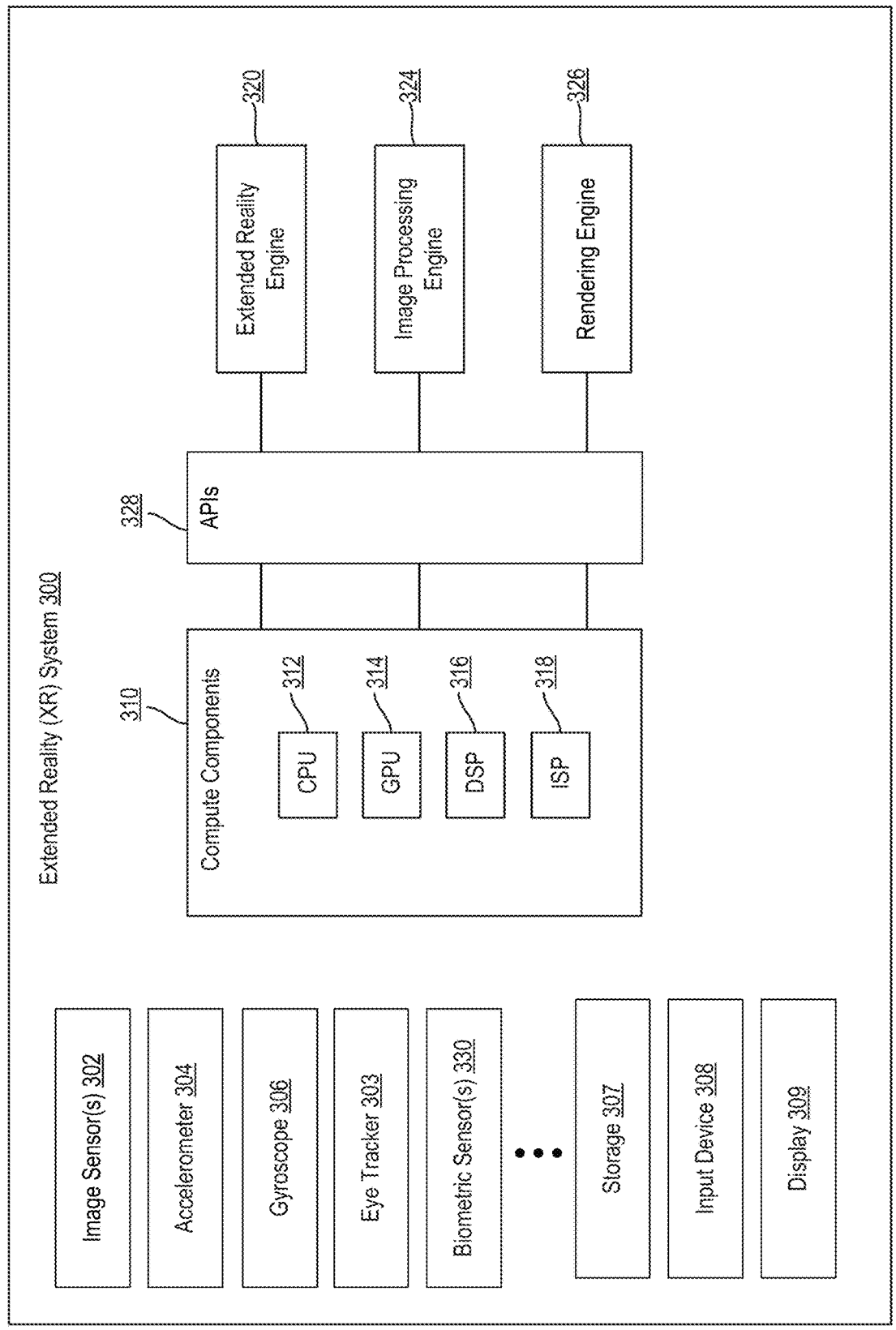
FIG. 3 is a diagram illustrating an architecture of an example extended reality (XR) system, in accordance with some examples.

FIG. 3 is a diagram illustrating an architecture of an example XR device 300, in accordance with some aspects of the disclosure. The XR device 300 can run (or execute) XR applications and implement XR operations. In some examples, the XR device 300 can perform tracking and localization, mapping of an environment in the physical world (e.g., a scene), and/or positioning and rendering of virtual content on a display 309 (e.g., a screen, visible plane/region, and/or other display) as part of an XR experience. For example, the XR device 300 can generate a map (e.g., a three-dimensional (3D) map) of an environment in the physical world, track a pose (e.g., location and position) of the XR device 300 relative to the environment (e.g., relative to the 3D map of the environment), position and/or anchor virtual content in a specific location(s) on the map of the environment, and render the virtual content on the display 309 such that the virtual content appears to be at a location in the environment corresponding to the specific location on the map of the scene where the virtual content is positioned and/or anchored. The display 309 can include a glass, a screen, a lens, a projector, and/or another display mechanism that allows a user to see the real-world environment and also allows XR content to be overlaid, overlapped, blended with, or otherwise displayed thereon.

In this illustrative example, the XR device 300 includes one or more image sensors 302, an accelerometer 304, one or more eye trackers 303, a gyroscope 306, storage 307, compute components 310, an XR engine 320, an image processing engine 324, a rendering engine 326, and one or more biometric sensors 330. In some aspects, the biometric sensor(s) 330 can include a PPG sensor, a pneumo-arterial plethysmography (PAPG) sensor, any combination thereof, and/or another type of sensor that can measure biometric information. In one illustrative example, the one or more biometric sensors 300 may include a microwave sensor that uses a plurality of complementary split-ring resonators to perform non-invasive measurements of blood, such as detecting blood flow and blood oxygen levels. In the example shown in FIG. 3, the engines 320-326 may access hardware components, such as components 302-318, or another engine 320-326 via one or more application programming interfaces (APIs) 328. Generally, APIs 328 are a set of functions, services, and/or interfaces, which act as a connection between computer components, computers, or computer programs. The APIs 328 may provide a set of API calls that may be accessed by applications that allow information to be exchanged, hardware to be accessed, or other actions to be performed.

It should be noted that the components 302-328 shown in FIG. 3 are non-limiting examples provided for illustrative and explanation purposes, and other examples can include more, less, or different components than those shown in FIG. 3. For example, in some cases, the XR device 300 can include one or more other sensors (e.g., one or more inertial measurement units (IMUs), radars, light detection and ranging (LIDAR) sensors, radio detection and ranging (RADAR) sensors, sound detection and ranging (SODAR) sensors, sound navigation and ranging (SONAR) sensors. audio sensors, etc.), one or more display devices, one more other processing engines, one or more other hardware components, and/or one or more other software and/or hardware components that are not shown in FIG. 3. While various components of the XR device 300, such as the accelerometer 304, may be referenced in the singular form herein, it should be understood that the XR device 300 may include multiple of any component discussed herein (e.g., multiple accelerometers 304).

The XR device 300 includes or is in communication with (wired or wirelessly) an input device 308. The input device 308 can include any suitable input device, such as a touchscreen, a pen or other pointer device, a keyboard, a mouse button or key, a microphone for receiving voice commands, a gesture input device for receiving gesture commands, a video game controller, a steering wheel, a joystick, a set of buttons, a trackball, a remote control, any other input device discussed herein, or any combination thereof. In some cases, one or more image sensors 302 can capture images that can be processed for interpreting gesture commands.

In some implementations, the one or more image sensors 302, the accelerometer 304, the gyroscope 306, storage 307, eye tracker 303, compute components 310, XR engine 320, image processing engine 324, and rendering engine 326 can be part of the same computing device. For example, in some cases, the one or more image sensors 302, eye trackers 303, the accelerometer 304, the gyroscope 306, storage 307, compute components 310, APIs 328, XR engine 320, image processing engine 324, and rendering engine 326 can be integrated into an HMD, extended reality glasses, smartphone, laptop, tablet computer, gaming system, and/or any other computing device. However, in some implementations, the one or more image sensors 302, eye trackers 303, the accelerometer 304, the gyroscope 306, storage 307, compute components 310, APIs 328, XR engine 320, image processing engine 324, and rendering engine 326 can be part of two or more separate computing devices. For example, in some cases, some of the components 302-226 can be part of or implemented by, one computing device, and the remaining components can be part of or implemented by, one or more other computing devices.

The storage 307 can be any storage device(s) for storing data. Moreover, the storage 307 can store data from any of the components of the XR device 300. For example, the storage 307 can store data from the one or more image sensors 302 (e.g., image or video data), data from the eye trackers 303 (e.g., eye tracking data) data from the accelerometer 304 (e.g., measurements), data from the gyroscope 306 (e.g., measurements), data from the compute components 310 (e.g., processing parameters, preferences, virtual content, rendering content, scene maps, tracking and localization data, object detection data, privacy data, XR application data, face recognition data, occlusion data, etc.), data from the XR engine 320, data from the image processing engine 324, and/or data from the rendering engine 326 (e.g., output frames). In some examples, the storage 307 can include a buffer for storing frames for processing by the compute components 310.

The one or more compute components 310 can include a CPU 312, a GPU 314, a DSP 316, an ISP 318, and/or other processor (e.g., a neural processing unit (NPU) implementing one or more trained neural networks). The compute components 310 can perform various operations such as image enhancement, computer vision, graphics rendering, extended reality operations (e.g., tracking, localization, pose estimation, mapping, content anchoring, content rendering, etc.), image and/or video processing, sensor processing, recognition (e.g., text recognition, facial recognition, object recognition, feature recognition, tracking or pattern recognition, scene recognition, occlusion detection, etc.), trained machine learning operations, filtering, and/or any of the various operations described herein. In some examples, the compute components 310 can implement (e.g., control, operate, etc.) the XR engine 320, the image processing engine 324, and the rendering engine 326. In other examples, the compute components 310 can also implement one or more other processing engines.

The one or more image sensors 302 can include any image and/or video sensors or capturing devices. The one or more image sensors 302 can include one or more user-facing image sensors. In some cases, user-facing images sensors can be included in the one or more image sensors 302. In some examples, user-facing image sensors can be used for face tracking, eye tracking, body tracking, and/or any combination thereof. The one or more image sensors 302 can include one or more environment facing sensors. In some cases, the environment facing sensors can face in a similar direction as the gaze direction of a user. In some examples, the one or more image sensors 302 can be part of a multiple-camera assembly, such as a dual-camera assembly. The one or more image sensors 302 can capture image and/or video content (e.g., raw image and/or video data), which can then be processed by the compute components 310, the XR engine 320, the image processing engine 324, and/or the rendering engine 326 as described herein. In some examples, the image sensors 302 may include an image capture and processing system 200, an image capture device 205A, an image processing device 205B, or a combination thereof.

In some examples, one or more image sensors 302 can capture image data and can generate images (also referred to as frames) based on the image data and/or can provide the image data or frames to the XR engine 320, the image processing engine 324, and/or the rendering engine 326 for processing. An image or frame can include a video frame of a video sequence or a still image. An image or frame can include a pixel array representing a scene. For example, an image can be a red-green-blue (RGB) image having red, green, and blue color components per pixel; a luma, chroma-red, chroma-blue (YCbCr) image having a luma component and two chroma (color) components (chroma-red and chroma-blue) per pixel; or any other suitable type of color or monochrome image.

In some cases, one or more image sensors 302 (and/or other camera of the XR device 300) can be configured to also capture depth information. For example, in some implementations, one or more image sensors 302 (and/or other camera) can include an RGB-depth (RGB-D) camera. In some cases, the XR device 300 can include one or more depth sensors (not shown) that are separate from one or more image sensors 302 (and/or other camera) and that can capture depth information. For instance, such a depth sensor can obtain depth information independently from one or more image sensors 302. In some examples, a depth sensor can be physically installed in the same general location as one or more image sensors 302 but may operate at a different frequency or frame rate from one or more image sensors 302. In some examples, a depth sensor can take the form of a light source that can project a structured or textured light pattern, which may include one or more narrow bands of light, onto one or more objects in a scene. Depth information can then be obtained by exploiting geometrical distortions of the projected pattern caused by the surface shape of the object. In one example, depth information may be obtained from stereo sensors such as a combination of an infra-red structured light projector and an infra-red camera registered to a camera (e.g., an RGB camera).

The XR device 300 can also include other sensors integral to one or more sensors. The one or more sensors can include one or more accelerometers (e.g., accelerometer 304), one or more gyroscopes (e.g., gyroscope 306), and/or other sensors. The one or more sensors can provide velocity, orientation, and/or other position-related information to the compute components 310. For example, the accelerometer 304 can detect acceleration by the XR device 300 and can generate acceleration measurements based on the detected acceleration. In some cases, the accelerometer 304 can provide one or more translational vectors (e.g., up/down, left/right, forward/back) that can be used for determining a position or pose of the XR device 300. The gyroscope 306 can detect and measure the orientation and angular velocity of the XR device 300. For example, the gyroscope 306 can be used to measure the pitch, roll, and yaw of the XR device 300. In some cases, the gyroscope 306 can provide one or more rotational vectors (e.g., pitch, yaw, roll). In some examples, the one or more image sensors 302 and/or the XR engine 320 can use measurements obtained by the accelerometer 304 (e.g., one or more translational vectors) and/or the gyroscope 306 (e.g., one or more rotational vectors) to calculate the pose of the XR device 300. The XR device 300 can also include the eye tracker 303 for tracking movement of the eyes of a user of the XR device 300. The eye tracker 303 of the XR device 300 may operate in a manner similar to eye tracking as described with respect to FIG. 1.

The output of one or more sensors (e.g., the accelerometer 304, the gyroscope 306, one or more IMUs, and/or other sensors) can be used by the XR engine 320 to determine a pose of the XR device 300 (also referred to as the head pose) and/or the pose of one or more image sensors 302 (or other camera of the XR device 300). In some cases, the pose of the XR device 300 and the pose of one or more image sensors 302 (or other camera) can be the same. The pose of image sensor 302 refers to the position and orientation of one or more image sensors 302 relative to a frame of reference (e.g., with respect to an object). In some implementations, the camera pose can be determined for 6-Degrees of Freedom (6DoF), which refers to three translational components (e.g., which can be given by X (horizontal), Y (vertical), and Z (depth) coordinates relative to a frame of reference, such as the image plane) and three angular components (e.g. roll, pitch, and yaw relative to the same frame of reference). In some implementations, the camera pose can be determined for 3-Degrees of Freedom (3DoF), which refers to the three angular components (e.g., roll, pitch, and yaw).

In some cases, a device tracker (not shown) can use the measurements from the one or more sensors and image data from one or more image sensors 302 to track a pose (e.g., a 6DoF pose) of the XR device 300. For example, the device tracker can fuse visual data (e.g., using a visual tracking solution) from the image data with inertial data from the measurements to determine a position and motion of the XR device 300 relative to the physical world (e.g., the scene) and a map of the physical world. As described below, in some examples, when tracking the pose of the XR device 300, the device tracker can generate a 3D map of the scene (e.g., the real world) and/or generate updates for a 3D map of the scene. The 3D map updates can include, for example, and without limitation, new or updated features and/or feature or landmark points associated with the scene and/or the 3D map of the scene, localization updates identifying or updating a position of the XR device 300 within the scene and the 3D map of the scene, etc. The 3D map can provide a digital representation of a scene in the real/physical world. In some examples, the 3D map can anchor location-based objects and/or content to real-world coordinates and/or objects. The XR device 300 can use a mapped scene (e.g., a scene in the physical world represented by, and/or associated with, a 3D map) to merge the physical and virtual worlds and/or merge virtual content or objects with the physical environment.

In some aspects, the pose of image sensor 302 and/or the XR device 300 as a whole can be determined and/or tracked by the compute components 310 using a visual tracking solution based on images captured by one or more image sensors 302 (and/or other camera of the XR device 300). For instance, in some examples, the compute components 310 can perform tracking using computer vision-based tracking, model-based tracking, and/or simultaneous localization and mapping (SLAM) techniques. For instance, the compute components 310 can perform SLAM or can be in communication (wired or wireless) with a SLAM system (not shown). SLAM refers to a class of techniques where a map of an environment (e.g., a map of an environment being modeled by XR device 300) is created while simultaneously tracking the pose of a camera (e.g., image sensor 302) and/or the XR device 300 relative to that map. The map can be referred to as a SLAM map and can be 3D. The SLAM techniques can be performed using color or grayscale image data captured by one or more image sensors 302 (and/or other camera of the XR device 300) and can be used to generate estimates of 6DoF pose measurements of one or more image sensors 302 and/or the XR device 300. Such a SLAM technique configured to perform 6DoF tracking can be referred to as 6DoF SLAM. In some cases, the output of the one or more sensors (e.g., the accelerometer 304, the gyroscope 306, one or more IMUs, and/or other sensors) can be used to estimate, correct, and/or otherwise adjust the estimated pose.

In some cases, the 6DoF SLAM (e.g., 6DoF tracking) can associate features observed from certain input images from one or more image sensors 302 (and/or other camera) to the SLAM map. For example, 6DoF SLAM can use feature point associations from an input image to determine the pose (position and orientation) of one or more image sensors 302 and/or XR device 300 for the input image. 6DoF mapping can also be performed to update the SLAM map. In some cases, the SLAM map maintained using the 6DoF SLAM can contain 3D feature points triangulated from two or more images. For example, key frames can be selected from input images or a video stream to represent an observed scene. For every key frame, a respective 6DoF camera pose associated with the image can be determined. The pose of one or more image sensors 302 and/or the XR device 300 can be determined by projecting features from the 3D SLAM map into an image or video frame and updating the camera pose from verified 2D-3D correspondences.

In one illustrative example, the compute components 310 can extract feature points from certain input images (e.g., every input image, a subset of the input images, etc.) or from each key frame. A feature point (also referred to as a registration point) as used herein is a distinctive or identifiable part of an image, such as a part of a hand, or an edge of a table, among others. Features extracted from a captured image can represent distinct feature points along three-dimensional space (e.g., coordinates on X, Y, and Z-axes), and every feature point can have an associated feature location. The feature points in key frames either match (are the same or correspond to) or fail to match the feature points of previously-captured input images or key frames. Feature detection can be used to detect the feature points. Feature detection can include an image processing operation used to examine one or more pixels of an image to determine whether a feature exists at a particular pixel. Feature detection can be used to process an entire captured image or certain portions of an image. For each image or key frame, once features have been detected, a local image patch around the feature can be extracted. Features may be extracted using any suitable technique, such as Scale Invariant Feature Transform (SIFT) (which localizes features and generates their descriptions), Learned Invariant Feature Transform (LIFT), Speed Up Robust Features (SURF), Gradient Location-Orientation histogram (GLOH), Oriented Fast and Rotated Brief (ORB), Binary Robust Invariant Scalable Keypoints (BRISK), Fast Retina Keypoint (FREAK), KAZE, Accelerated KAZE (AKAZE), Normalized Cross Correlation (NCC), descriptor matching, another suitable technique, or a combination thereof.

In some cases, the XR device 300 can also track the hand and/or fingers of the user to allow the user to interact with and/or control virtual content in a virtual environment. For example, the XR device 300 can track a pose and/or movement of the hand and/or fingertips of the user to identify or translate user interactions with the virtual environment. The user interactions can include, for example and without limitation, moving an item of virtual content, resizing the item of virtual content, selecting an input interface element in a virtual user interface (e.g., a virtual representation of a mobile phone, a virtual keyboard, and/or other virtual interface), providing an input through a virtual user interface, etc.

As noted above, in some cases, the one or more sensors can include at least one IMU. An IMU is an electronic device that measures the specific force, angular rate, and/or the orientation of the XR device 300, using a combination of one or more accelerometers, one or more gyroscopes, and/or one or more magnetometers. In some examples, the one or more sensors can output measured information associated with the capture of an image captured by one or more image sensors 302 (and/or other camera of the XR device 300) and/or depth information obtained using one or more depth sensors of the XR device 300.

The image sensors 302 of XR device 300 can include a gaze and/or eye tracker 303, such as the example discussed in FIG. 1. In some examples, the gaze and/or eye tracker 303 can obtain images of one or both of a user's eyes from user-facing image sensors of the one or more image sensors 302. As previously noted, in other examples, the XR device 300 can also include other sensors, such as an IMU, a magnetometer a machine vision sensor, a smart scene sensor, a speech recognition sensor, an impact sensor, a shock sensor, a position sensor, a tilt sensor, etc.

As described previously, XR devices and/or systems can facilitate interactions between users and content in the XR environment. It may be useful to have techniques to determine when a user is fatigued, not interested in, or is distracted from the XR environment. Generally, eye tracking can provide information regarding user attentiveness as the human eye has a relatively small area, or fovea, that has the highest visual acuity. Outside of a foveal area, visual acuity rapidly drops off. In some cases, foveated rendering may allow fovea areas of an image to be rendered with higher resolution than areas outside of the fovea areas (referred to as peripheral areas) that may be rendered with a lower resolution. In some cases, due to the higher resolution fovea areas and lower resolution peripheral areas, the eyes of a user may tend to move to focus the higher resolution foveal area towards environmental elements that are of interest. This eye movement may be due to either a conscious or unconscious decision of the user to look at the environmental elements. An amount of time and/or a number of times a user looks at an environmental element may indicate how much attention the user is paying to that environmental element. In accordance with aspects of the present disclosure, eye tracking data indicating which area(s) of an image at which a user is gazing may be compared to an ROI in the XR environment, or identified by the XR device, to determine information about user attentiveness to the XR environment.

In some aspects, the biometric sensor(s) 330 may be a PPG sensor disposed at a surface of the XR device 300 and interfaces with the user's skin. The biometric sensor(s) 330 may be configured to measure blood flow beneath the surface of the user's skin according to some aspects, and the measurements can be used to determine various physiological properties such as heart rate, blood pressure, and so forth. In some aspects, the biometric sensor(s) 330 configures an electrical path that can be used to form an electrical loop to form an electrocardiogram (ECG or EKG) sensor.

Figure 4:
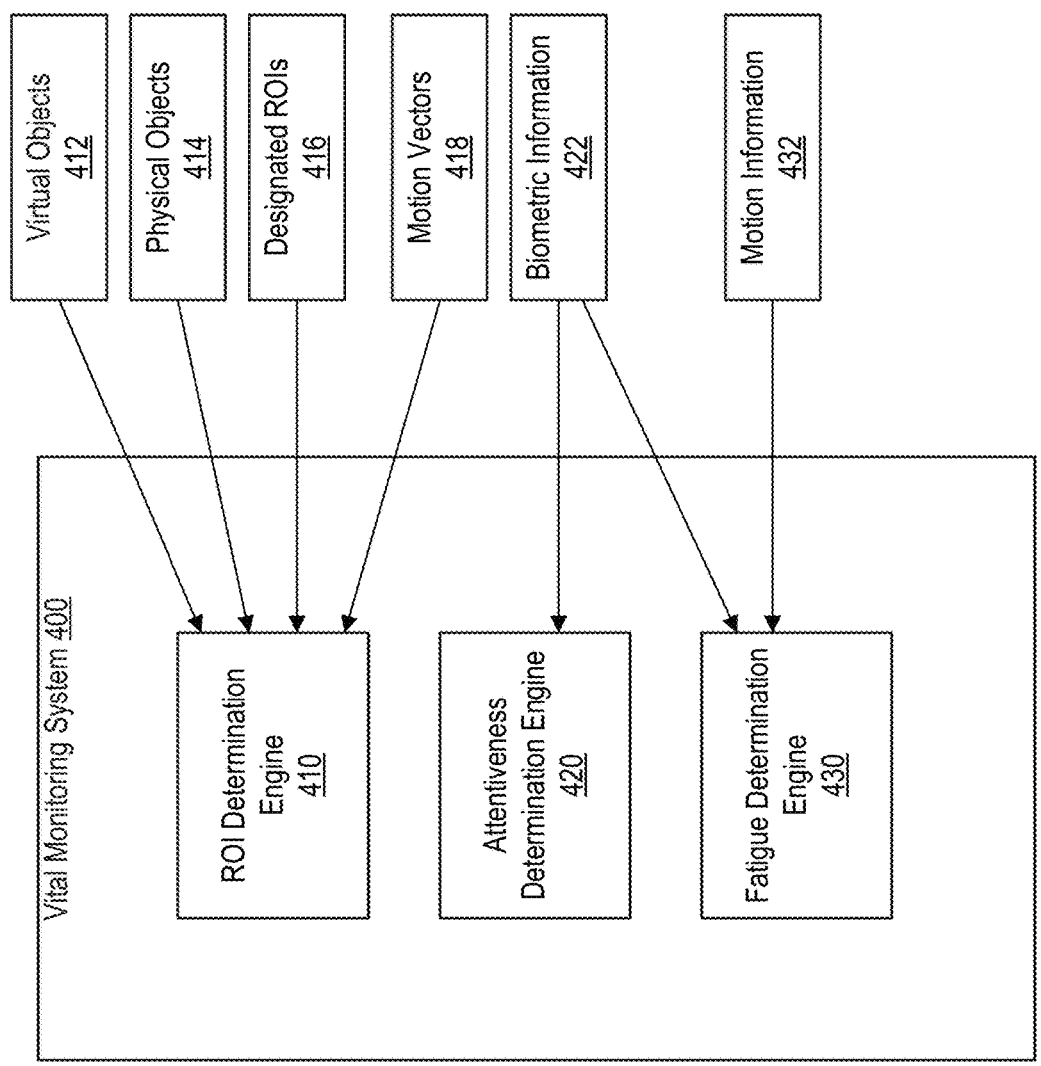
FIG. 4 is a block diagram illustrating an architecture of a physiological monitoring system for monitoring physiological information and attentiveness, in accordance with some examples.

FIG. 4 is a block diagram illustrating an architecture of a physiological monitoring system 400, in accordance with aspects of the present disclosure. In some cases, the physiological monitoring system 400 may be included in an XR device, such as XR device 300. The physiological monitoring system 400 may monitor physiological information (e.g., heart rate, blood pressure) of a person. In one example, a physiological monitoring system 400 can monitor physiological information of a user wearing an XR device (e.g., a user of the XR device). The physiological monitoring system 400 may monitor related information relevant to the physiological information of a person, such as the attentiveness of the person wearing the XR device. In some aspects, the physiological monitoring system 400 can include an ROI determination engine 410, an attentiveness determination engine 420, and a fatigue determination engine 430.

The ROI determination engine 410 is configured to determine one or more ROIs in the content presented to the user (e.g., one or more images displayed on a display for viewing by the user). As described herein, ROIs determined by the ROI determination engine 410 in the content are portions of the content or environment visible to a user (e.g., in a see-through or pass-through XR device) which are identified as likely to be of interest to the user. The ROI determination engine 410 may identify ROIs in a number of ways. In one example, virtual objects 418 or content that are superimposed/merged into a view of the environment (e.g., by displaying the virtual objects 418 with the view of the environment), either physical or virtual, may be identified as ROIs. Virtual objects 418 may be obtained, for example, from the rendering engine 326 or XR engine 320 of FIG. 3 via API calls. In some cases, physical objects 414 in the physical environment (e.g., physical objects that are near to or between a user and one or more virtual objects/content) may also be identified as ROIs. For example, the physical objects 414 may prevent or alter the way users properly or safely interact with the one or more virtual objects/content. Physical objects 414 may be detected in the physical environment as a part of, for example, merging and/or overlaying the XR environment with the physical environment. The ROI determination engine 410 may obtain these detected physical objects 414 from, for example, the XR engine 320 of FIG. 3 via API calls.

As another example, designated ROIs 416 may be identified by a creator of the content (referred to as a content creator). The designated ROIs 416 may be made available during execution time. For example, APIs for interfacing with graphic accelerators, such as GPUs, or for rendering may include one or more function calls that allow a particular object, pixels, area, etc., to be designated as an ROI. A content creator such as a game developer may then be able to designate, for example, a certain portion or multiple portions of a game object, such as important puzzle pieces, as an ROI during the development of the game. The designated ROI 416 may be accessed, for example, via an API call.

Generally, rendering images for display to a user rapidly becomes more computationally expensive as resolutions increase. One possible way to reduce the computational load on the system while still maintaining perceived resolution is to reduce the rendering resolution for portions of the image that the user is less likely to look at while maintaining or reducing the resolution to a lesser extent than for those areas the user is less likely to look at, the rendering resolutions for areas that the user is more likely to look at (e.g., the ROIs). By rendering the ROIs in a higher resolution than areas that are less likely to be looked at by a user, there may be less of a user perceived quality degradation, for example, when combined with adjusting the rendering resolution based on eye tracking data (e.g., foveated rendering). As the initial rendering resolution of the ROIs is already higher, when foveated rendering is used, there is less of a shift in rendering resolution that could be perceived by the user as they look around. These designated ROI 416 may be made available (e.g., by an API call during runtime) to other programs (e.g., from the rendering engine 326 or GPU 314). Alternatively, or in addition, the rendering engine 326 of FIG. 3 may detect the areas which are rendered in a higher resolution than other areas and report those areas as designated ROIs 416.

In another example, the ROI determination engine 410 may analyze various aspects of the image for display to the user to determine ROIs in the image. For example, where designated ROI 416, virtual objects 418, and physical objects 414 information is not available, the ROI determination engine 410 may access one or more of the images generated for display to the user from, for example, the GPU 314 and perform object detection on the images. The ROI determination engine 410 may perform object detection using any type of object detection algorithm, including, but not limited to facial recognition, object recognition, feature recognition, tracking or pattern recognition algorithms, etc. Areas corresponding to detected objects, or a certain type of a detected object, such as faces, animals, etc., may be determined to be an ROI.

In another example ROI determination technique, the ROI determination engine 410 may analyze the images for converging lines. Converging lines in the content may draw attention of a user to an area where the lines converge. The ROI determination engine 410 may thus determine an area of an image with such converging lines as an ROI.

As another example, an ROI determination technique applied by the ROI determination engine 410 may be based on portions of the images that are blurred or not in focus or are of a lower resolution as compared to other portions of an image (e.g., based on foveated rendering). For example, the ROI determination engine 410 may determine areas that are blurred (or are in focus) as ROI(s). In another example, the ROI determination engine 410 may determine areas in an image that are of a higher resolution (as compared to other areas of the image) as ROIs.

In some cases, the ROI determination engine 410 may determine an ROI based on information from multiple images. For example, motion vectors may be determined between multiple image frames for pixels or groups of pixels. The ROI determination engine 410 may compare the motion vectors across pixels or groups of pixels from the different image frames to determine whether particular pixels or groups of pixels move (or move greater than a threshold amount of motion) relative to the other pixels or groups of pixels. The ROI determination engine 410 may determine areas exhibiting more motion (e.g., more than the threshold amount of motion) as ROI(s).

In some cases, rendering of the images displayed to the user may be performed by a computing device separate from another computing device that displays the images to the user. In such cases, the images may be compressed, for example as a compressed video stream. In some cases, ROI information may be determined based on properties of the compressed image data (e.g., frames or pictures of a compressed video stream) by the computing device receiving and decompressing the video stream. For example, video is often compressed using a set of reference frames (or keyframes) and motion vectors (e.g., motion vectors 418). The motion vectors 418 describe how blocks of pixels move in comparison to a reference frame. The motion vectors 418 can be used to determine areas in the video stream that exhibit more motion than other areas. The ROI determination engine 410 may determine that areas exhibiting more motion (e.g., an amount of motion greater than the threshold amount of motion) are ROIs.

In some cases, ROI determination engine 410 may include or use a machine learning (ML) system or technique (e.g., a deep learning, such as one or more neural networks) to determine that an area in an image is an ROI. The ML system may use as input information from any of the above-described examples, such as motion vectors, or any other type of information, and generate predictions of where one or more ROIs are for images to be displayed to the user. In some cases, multiple ML systems may be used by the ROI determination engine 410. For example, an ML system may be trained to generate ROI predictions based on motion vectors, while another ML system may be trained to generate ROI predictions based on recognized objects, etc. Multiple ML systems may also be chained in some aspects. In some cases, the ML system may take multiple types of information to generate predictions. For example, an ML system may be trained to determine an ROI based on motion vectors, focused areas (areas of an image that are in focus as compared to other areas of the image), and/or detected objects. In some cases, a combination of multiple techniques may be used to determine an ROI.

After one or more ROIs are identified by the ROI determination engine 410, information associated with the identified ROIs may be transmitted to the attentiveness determination engine 420. In one aspect, biometric information 422 provided by a biometric sensor can be provided to the attentiveness determination engine 420. For example, the biometric information 422 can include eye-tracking information that is provided by an eye-tracking sensor (e.g., the eye tracker 303 described above in FIG. 3). The attentiveness determination engine 420 may compare the identified ROIs to eye-tracking information included in the biometric information 422. In one illustrative aspect, the attentiveness determination engine 420 determines whether the user is focused on the content being displayed based on comparing the identified ROIs to the eye-tracking information.

Various biometric information 422 can be used by the attentiveness determination engine 420 to determine the attentiveness of the user. Non-limiting examples of biometric information include eye information, cardiovascular information, respiratory information, and other information that can be detected or derived from one or more sensors (e.g., a sensor of the XR device or a device connected to the XR device. The eye information can be provided by an eye sensor that is configured to sense pupil size, blinking, oculomotor-based metrics, gaze allocation, eye movement directions, and saliency. In one aspect, a plurality of sensors can form an electrical loop that includes the heart in the path of the electrical loop for implementing an electrocardiographic (EKG) sensor.

In some aspects, cardiovascular information comprises various information related to the blood such as heart rate (e.g., pulse rate), respiratory rate, blood pressure, oxygen level, body temperature, and so forth. The cardiovascular information can be vital information derived by the sensor (e.g., the heart rate in numerical form) or can be a sensor for deriving corresponding vital information (e.g., a series of images or data that can be used by a processor to derive a numerical heart rate).

Figure 6A:
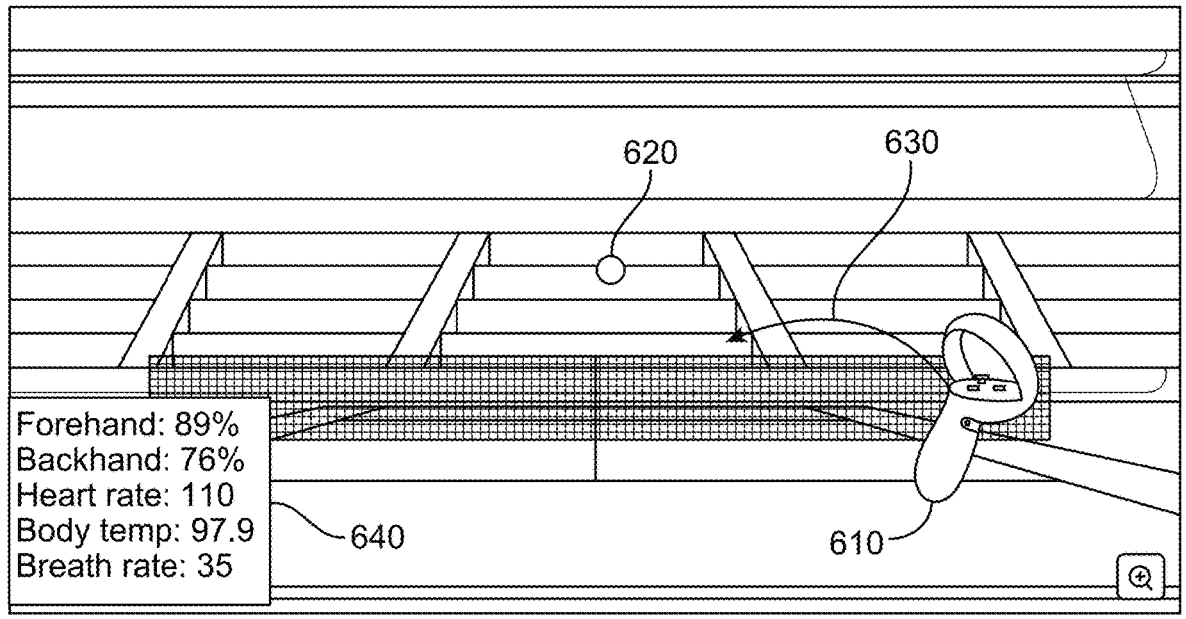
FIGS. 6A-6B are conceptual illustrations of a virtual application that can be executed by an XR device, in accordance with some aspects of the disclosure.

In some aspects, the cardiovascular information can be provided from an external device that is connected to the XR device. Non-limiting examples of an external device include a watch that includes at least one biometric sensor (e.g., a network-connected watch, or so-called "smartwatch", with a PPG sensor), a controller device that is used by the user to perform various inputs, and so forth. In one aspect, the XR device may be wirelessly connected to a controller, such as an XR game controller. An example of an XR game controller is illustrated in FIG. 6A and is configured to detect 6DoF of motions (e.g., translational movement in cartesian coordinates and rotational movement such as roll, pitch, and yaw). The XR game controller can include one or more biometric sensors such as a PPG sensor to detect the cardiovascular information. In another aspect, the XR device may be connected to a sensor integral to an external component, such as headphones or earphones, and can provide an electrical contact point for the XR device. In one illustrative example, the earphones can include an electrical contact that contacts a user's inner ear canal and can be used to form an electrical loop through the heart of the user to perform EKG measurements.

The fatigue determination engine 430 may use additional information included within the biometric information, such as the cardiovascular information that can be detected using a PPG sensor (e.g., the biometric sensor(s) 330 described above in FIG. 3). As described above, the cardiovascular information can include vital information (e.g., a heart rate, a blood pressure) or include sensor information that can be processed to determine the vital information.

In one aspect, the physiological monitoring system 400 may also include a fatigue determination engine 430 for receiving the biometric information 422 and motion information 432 and determining the fatigue of the user. In one aspect, an XR device may execute an application that directs movement (e.g., a directed movement application) of a user for various purposes, and the fatigue determination engine 430 may be used to identify fatigue and other pertinent information usable by the virtual application. For example, the directed movement application directs a user to perform various movements to improve cardiovascular and physiological health of the user. The fatigue determination engine 430 can provide fatigue information to the virtual application and cause the virtual application to customize the movement performed by the user based on fatigue. In another aspect, a virtual application directs movement of a user and encourages a user to perform exercises that improve various movements that can be applied to a sport. For example, the virtual application can be a sport-specific training application such as golf or tennis. The virtual application may be configured to identify mobility limitations (e.g., hip flexibility) based on fatigue and identify movements to address the mobility limitations.

The motion information 432 may include various aspects of motions that are detectable by the XR device and/or by other devices that are connected to the XR device. Non-limiting examples of motion include a motion (e.g., a path) traversed by a limb of the user or a motion of the user, characteristics of the motion such as acceleration, jerk, rotation, and so forth. In some aspects, the motion information 432 may include that indicates an orientation of the user (e.g., the user is leaning forward and balancing on the front of their foot, or the user is in a prone position). The motion information can also be used to derive various properties, such as the duration of the movement, joint mobility limitations that cause various defects with a corresponding motion, and so forth. For example, the virtual application may identify movement defects related to joint mobility and can provide additional directed movements to improve joint mobility.

In some aspects, the fatigue determination engine 430 is configured to receive the motion information 432 that includes motion information related to movements that the user is performing. The motion information 432 can be obtained directly from the XR device, such as an XR device 300 having various sensors. For example, the XR device 300 can obtain motion information from various sensors including the accelerometer 304 and the gyroscope 306. In further aspects, the XR device can also obtain motion information for an external device that is configured to provide information to the XR device. In one aspect, the XR device may be wirelessly connected to a controller, such as an XR game controller. An example of an XR game controller is illustrated in FIG. 6A and is configured to detect 6DoF of motions (e.g., translational movement in cartesian coordinates and rotational movement such as roll, pitch, and yaw). A user of the XR device may hold one or more XR game controllers and physically move the XR game controllers, which is then detected and translated into the motion information 432. The XR game controllers provide the motion information 432 to the XR device. The motion information 432 can be provided from a device attached to the user that includes one or more motion sensors. For example, a smartwatch may include one or more motion sensors such as an accelerometer, a gyroscope, and so forth.

In some aspects, the physiological monitoring system 400 may also be configured to receive externally provided biometric information 422 and/or motion information 432. For example, as described below, an XR game controller, a smartwatch, or other device can be configured to connect to the XR device to provide externally monitored motion information and/or biometric information.

In some aspects, the XR game controllers may also include a biometric sensor and provide the biometric sensor to the XR device. For example, the XR game controller can include a PPG sensor that interfaces with the user (e.g., the user of the XR device) to detect biometric information, such as blood pressure, and heart rate. In some aspects, a device attached to the user can also include a biometric sensor and/or other sensors. For example, a smartwatch can include a PPG sensor that contacts the skin of the user and provides the biometric sensor to the XR device.

Based on the motion information 432 and the biometric information 422, the fatigue determination engine 430 can determine the fatigue information of the user and store fatigue information in a profile associated with a user. In some cases, the fatigue information can include fatigue level information, which provides different fatigue amounts. For example, the physiological monitoring system 400 may be configured to transmit at least a portion of the fatigue information and other vital information to a monitoring service. The monitoring service can be configured to provide the fatigue information, physiological information, and other vital information into a rule-based module and/or ML model to monitor the user's vital information during the directed movement. In some cases, the rule-based module and/or ML model can be trained to identify potential health issues and monitor the user's activity. For example, the vital information can identify defects in the user's heartbeat indicative of critical health issues. In other aspects, the ML model can identify potential issues based on trends that could result in dangerous side effects, such as the user losing consciousness, dehydration, adverse heat-related issues (e.g., a heat stroke), and so forth. The rule-based model can identify other issues such as overexertion based on rules such as a maximum heart rate, which can be based on the user's profile. In some cases, the user's profile can include various health-related information (age, height, weight, previous motion information, joint issues, etc.) that can be used by the monitoring service and/or the virtual application to identify adverse fatigue effects. For example, the virtual application can identify that the user may be at risk of losing consciousness based on heart rate and blood pressure, which could adverse issues (e.g., the user falling).

In some aspects, the fatigue information can be related to information provided by other sensors, such as the eye sensor. In one illustrative aspect, the fatigue determination engine 430 is configured to detect fatigue based on a deformation of an eye of the user, such as when an eye bulges. Other eye information pertinent to fatigue includes pupil measurements, blinking, oculomotor-based metrics, gaze allocation, eye movement directions, and a saliency mode.

In some other aspects, the fatigue determination engine 430 is also configured to detect fatigue based on the attentiveness of the user. For example, the user's lack of focus on an ROI can be indicative of one or more types of fatigue. The level of fatigue can be directly related to the duration of the lack of focus. For example, if the user is becoming tired, the user may lose focus for a small period of time (e.g., 5 seconds). In another example, if the user is exhausted and may need to stop the exercise, the user can lose focus for a longer period of time (e.g., 15 seconds). In some aspects, the fatigue determination engine 430 can be configured to guide the focus of the user to correct form based on head position by overlaying a graphical demarcation on an object within the virtual application and can determine an amount of fatigue based in part of the user losing focus.

Fatigue can come in different variants, such as cardiovascular fatigue, movement fatigue, nervous system fatigue, and interest fatigue, and in some cases, the various fatigues can be correlated. In some aspects, the physiological monitoring system 400 collections biometric information and user activity information and can determine detailed fatigue information. The user activity information can include fatigue detection detail, interest level information, heart rate, blood pressure, oxygen level, body temperature, and other activities of one or more users.

In some other aspects, the fatigue determination engine 430 is also configured to detect fatigue based on the attentiveness of the user. For example, the user's lack of focus on an ROI can be indicative of one or more types of fatigue. In one illustrative aspect, the fatigue determination engine 430 can identify that the ROI of the user is defocused with respect to a pertinent user interface (UI) feature within the virtual application. For example, the user may be requested to focus on a particular spot for a movement to improve balance and form, and a different ROI can indicate that the user's lack of focus is indicative of fatigue. In some cases, some movements can tax the central nervous system differently in a manner that does not exhaust the cardiovascular system, and fatigue from these movements can be identified despite the cardiovascular measurements not indicating exhaustion.

In other aspects, the lack of focus can also indicate interest fatigue, or the user of the XR device being uninterested or unmotivated in the directed movement. For example, if the user's focus is different from an ROI for a sufficiently long duration, the user may be fatigued and/or has a low interest in the directed movement.

In further aspects, the fatigue determination engine 430 is also configured to detect fatigue due to motion fatigue for a particular type of directed movement. In some aspects, the fatigue determination engine 430 can identify a particular repetitive motion that indicates exhaustion of a particular muscle group. For example, the fatigue determination engine 430 may determine that pushup takes more than 5 seconds indicates the user is exhausted from this particular exercise. In some aspects, if no motion or a low volume of motion is detected for the directed movement that includes a large volume of motion, the fatigue determination engine 430 may determine the user has a low interest.

In some aspects, an EKG sensor can be configured based on creating an electrical loop that passes the heart. For example, an XR game controller with an electrical interface (e.g., a PPG sensor) that is connected via a wire to an XR device that includes an electrical interface (e.g., a PPG sensor) forms an electrical loop from the user's hand to the user's head, and the electrical loop passes through the heart. In some aspects, an EKG sensor is formed by at least two touch points electrically connected by a wire that a path between the two touch points passes through the heart of the user. For example, a smartwatch having a PPG sensor can form a path with a metal button that is touched by a user's hand.

According to various aspects, the physiological monitoring system 400 may be configured to store physiological information in a user profile, as well as other biometric information such as age, weight, and so forth. The physiological monitoring system 400 may be configured to use the user profile to monitor the user's activity based on prior activity that incorporates the XR device. In some cases, a usage gap between a user's detected physiological information as compared to the stored physiological information, the physiological monitoring system 400 may alert the user regarding changes. For example, if a user enters an XR environment and has a lower resting heart rate, the XR environment can alert the user to the change within the XR environment.

Based on the fatigue information, an XR device including the physiological monitoring system 400 may be configured to display the measured physiological information and provide that physiological information to the user. For example, the heart rate of the user can be detected and output by the physiological monitoring system 400. In another illustrative aspect, the XR device including the physiological monitoring system 400 may be configured to provide interactive information such as an avatar that represents the user, and the avatar is modified based on a plurality of characteristics associated with fatigue. For example, if the physiological monitoring system 400 identifies that the user is tired due to lack of oxygen due to cardiovascular exertion, the XR device including the physiological monitoring system 400 may be configured to display the avatar as winded and breathing heavily. In another example, if the XR device including the physiological monitoring system 400 identifies that a muscle group is fatigued, the XR device including the physiological monitoring system 400 can output a visual depiction of the avatar that emphasizes that a muscle group is fatigued.

Further aspects of the XR device include determining a corrective action based on the fatigue information. In one illustrative aspect, the fatigue information can identify that the user is fatigued based on strenuous physical exertion, for example, the user's heart rate is greater than 90% of the maximum heart rate for a period of time. In response to detecting user fatigue, the XR device can cause the user to rest by changing to a different exercise that is less intense or scaling a movement or exercise. In one example, a corrective action may be a recovery action the user partakes in to decrease cardiovascular exertion effects. Non-limiting examples of a recovery action can be timed breathing, meditation, or a resting pose that encourages joint mobility. In some aspects, the resting pose can be a yoga pose or other active stretch that increases mobility and allows cardiovascular recovery. Examples of a resting pose include child pose, but can be more active such as a hip mobility stretch, and so forth. Scaling the exercise includes reducing the difficulty of the exercise, such as reducing the range of movement.

One example of a resting pose includes various yoga poses such as child pose. In some cases, the resting pose may be an active stretch to encourage joint mobility. In one aspect, the corrective action may be to disengage the user from a usage instance of the XR device (e.g., from an application of the XR device) and uses heavy movement inputs.

Another aspect includes physiological-based re-engagement of the XR device. In one aspect, after disengagement due to fatigue, the XR device may be configured to measure physiological information (e.g., heart rate, blood pressure, respiratory rate, etc.) and enable the XR device after the user has sufficiently rested. The XR device can be configured to allow the user to reengage based on passing one or more physiological measurements that are indicative of the user being rested. For example, the heart rate may recover in a short period of time, but blood pressure has a longer recovery period. In this case, the XR device is configured to allow the user to reengage based on a heart rate and blood pressure being lower that particular threshold. In some cases, a non-linear weight can be applied to the physiological measurements. For example, if the heart rate of the user is below 100 PPM, the weight of the heart rate may be equal to the weight of the blood pressure, and if the heart rate of the user is below 120 PPM, the weight of the heart rate has less weight than the weight of the blood pressure.

In other aspects, the XR device can be configured to encourage usage of the virtual application based on providing rewards to stimulate usage. For example, the virtual application can be an exercise game that requires the user to perform exercises with the XR device to improve cardiovascular health and joint mobility. For example, when a user uses the virtual application 7 days in a row for at least 20 minutes can be provided an award that is redeemed within the virtual application. Rewards can be tailored in a manner that encourages improved health, such as proving rewards when the user reengages.

In another aspect of the disclosure, when more than one Wi-Fi radios are available in an XR environment, channel capture could be used to capture channel state information (CSI) and perform sensing. When only a single Wi-Fi radio is available, Wi-Fi Radar could be used to capture CSI and perform sensing. In one aspect, channel capture and Wi-Fi Radar can be used to capture CSI and perform sensing to calculate the user's breathing rate.

Further aspects of the disclosure relate to user activity classification based on determining a combined estimated fatigue using a plurality of weighted characteristics. In one aspect, fatigue detection can be based on eye information from an eye sensor, and each property of the eye information can be weighted. Non-limiting examples of properties measured by the eye sensor include pupil measurements, a blinking rate, oculomotor-based metrics, gaze allocation, eye movement directions, a saliency model, etc. In one illustrative example, the weighted properties can be accumulated over a period of time, either a fixed period (e.g., every 30 seconds) or a sliding window (e.g., cumulative measurements over a fixed period of time that exceed). For example, the pupil measurements can include the dilation (e.g., the radius or the diameter) of the user's pupil. The blinking rate can be the rate at which the user is blinking their eyes. The oculomotor-based metrics can include fixations and saccades, such as phases of slow and fast eye movements, respectively. The gaze allocation can include temporal patterns of eye movements in relation to action. The eye movement direction can include the motion of the eyes between salient regions. The saliency can include a model that predict the salient regions.

The fatigue level can be classified into levels, with each level corresponding to a different corrective event. In one example, if the combined estimated fatigue reaches a first threshold (Th1) for a period of time t1 or reaches the first threshold Th1 multiple times inside time duration t4, the user can be alerted (e.g., a visual or audio alert). If the combined estimated fatigue reaches a second threshold (Th2) for a period of t2 time or repetitively reaches the second threshold Th2 multiple times inside time duration t5, an XR device can be stopped the virtual reality application and display a prompt for user consent to continue. If the combined estimated fatigue reaches a third threshold (Th3) for a period of t3 time or repetitively reaches third threshold Th3 multiple times inside time duration t6, the server can be notified with fatigue detection. In some aspects, the server application may have a control to disengage the user. In some aspects, the second threshold Th2 is greater than the first threshold, and the third threshold Th3 is greater than the second threshold.

In some aspects, a level of interest can be determined based on a time period in which the user is out-of-focus and provided with visual feedback information. In some aspects, the visual feedback information is displayed to the user of the XR device and may provide a plurality of properties to enable the user to understand their fatigue. In one aspect, the visual feedback information can include the temperature of the wearer, the respiratory condition of the wearer, the focus of the wearer, or the exhaustion of a muscle or muscle group of the user. For example, if the user is winded due to strenuous cardiovascular activity, the avatar can be depicted as winded and breaking hard. An example of fatigue of a muscle or muscle group can be an animation that indicates the muscle group is tired such as the avatar massaging the muscle, or the muscle is depicted in a particular color to indicate the muscle is tired.

In one aspect, if the out-of-focus period is greater than a first time, lower user interest is detected, and the user can be alerted (e.g., by outputting an audio and/or visual alert) with corresponding visual feedback information. If the out-of-focus period is greater than a second time (which is longer than the first time), the XR device can stop and prompt for user consent to continue. If the out-of-focus period is greater than a third time (which is greater than the second time), the server can be notified with fatigue detection. The server application may have a control to disengage the user from the virtual application being executed in the XR device.

Each of the parameters described above (e.g., the first time, the out-of-focus period, etc.) may be adaptively determined based on the usage environment and the user's profile. For example, the user's age, medical condition, and historical record can be used to determine the various parameters. In some other aspects, the thresholds can be adapted based on the type of XR application. For example, fast-paced and competitive games may have higher thresholds for the user's heart rate. In some cases, the user profile can include historical records such as heart rates for similar games that were executed in the past. Other aspects of the user profile can include eye conditions such as eyesight, pupil measurements, etc.

In some aspects, a health monitoring service can be utilized by the XR device to assist in the detection of fatigue. In one illustrative aspect, the XR device can include an ML model that receives the physiological information, which has been randomized to comply with privacy regulations and predicts adverse health effects, such as loss of consciousness, heat strokes, and other effects. In some aspects, fatigue information and user interest level information (e.g., information ascertained based on out-of-focus duration) can be embedded with motion information and provided to the health monitoring service over an access point (AP). In some cases, the fatigue information and user interest level information can be provided in block acknowledgment (ACK). For example, the user activity information (which includes physiological information and motion information) and be provided in an uplink (UL) block ACK information subfield. The block ACK control can be used to indicate the user activity information data in the frame. The user activity information can be provided in other information sent to the health monitoring service.

In some aspects, the XR device can be configured to provide information over a cellular communication system such as 4G, 5G, and the like. For example, the fatigue detection information and user interest level information can be embedded with motion information to server over 5G to a next generation node B (gNB). In one example, thermal information (e.g., body temperature) can be sent in radio resource control (RRC) messages, which may be ideal to get information to both the edge and/or health monitoring service.

In some cases, the health monitoring service can also provide information to the XR device, such as warning information about potential adverse effects. The health monitoring service can also be configured to provide UI content to the XR device, such as avatar variants for each user that vary based on a plurality of properties. For example, the XR device can store avatars corresponding to different levels of users, user interest level, blood pressure, oxygen level, body temperature, and so forth. In one example, the avatar of user 1 has a unique identifier A1 and the health monitoring service may have 3 or different variants for A1 called (A1+F1), (A1+F2), (A1+F3). In this, F1, F2, and F3 are different fatigue levels and/or different interest level information for user 1. The XR device of the health monitoring service may be configured to update the avatar including periodicity and levels, and the avatar can be updated based on user configuration.

For example, after the user activity change, the health monitoring service should update the avatar based on the various information described above, and send the updated avatar in a subsequent downlink frame. In some aspects, the fatigue level, interest level, heart rate, blood pressure, oxygen level, and body temperature information can be conveyed without the avatar as well. In another aspect, the health monitoring service may indicate or notify VR users about fatigue/interest level information with textual content representation in the subsequent downlink frame. The health monitoring service may indicate or notify VR users about fatigue/interest level information with animation over the user 1 avatar and/or when hovering or focused on the avatar in the subsequent downlink frame. In case of split rendering, and if user activity is critical for the application, the update of the avatar should be performed by the local device (e.g., the XR device).

Other aspects include monitoring the user based on health issues. For example, if a second user is identified with blood pressure, heart rate, oxygen level, body temperature and/or fatigue level greater than a threshold level, the information can be indicated to the user's other health monitoring devices in a network and/or applications with scene information. Examples of scene information include time spend in a virtual application of the XR device, virtual application details, and context of the virtual application which can be used to characterize and understand the user's health analysis. The long-term data of user health behavior observation against the context can be used to take preventive actions in the future, or exercises and movement can be tailored based on the health of the user.

The virtual avatar in the virtual application can display properties corresponding to the user's physiological information, fatigue detection detail, and interest level information. Each physiological information feature may have unequal weights based on the virtual application scenario. For example, if a higher heart rate for a user is detected, the XR device can slow the pace of the virtual application.

Figure 5:
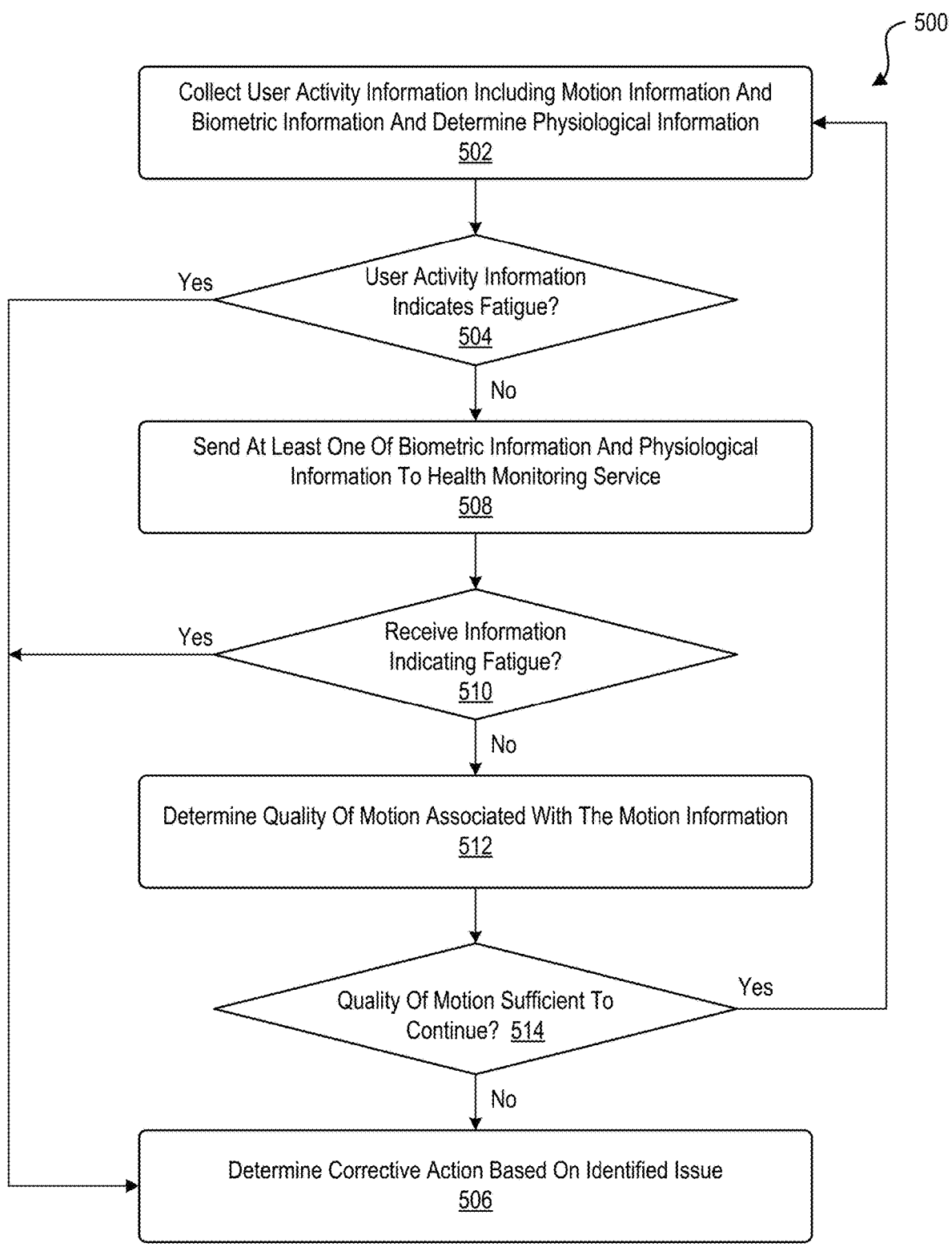
FIG. 5 is a flow diagram illustrating a technique for evaluating user fatigue and corrective measures, in accordance with aspects of the present disclosure.

FIG. 5 is a flowchart illustrating an example of a method 500 for monitoring activity of a person, in accordance with certain aspects of the present disclosure. The method 500 can be performed by an XR device or a computing device (or a component of the computing device) connected to an XR device, such as a mobile wireless communication device, a smart speaker, a camera, a wireless-enabled vehicle, or another computing device. In one illustrative example, a computing system 1000 can be configured to perform all or part of the method 500.

At block 502, the computing system may collect user activity information and determine whether the user activity information indicates fatigue. As described above, the user activity information can include biometric information (e.g. heart rate, blood pressure, various eye characteristics, etc.) and motion information. In some cases, the biometric information can include eye tracking information (e.g., from the eye trackers 303) that can be used to determine interest level.

At block 504, the computing system may determine if the user activity information indicates fatigue of the user. In some aspects, fatigue can be detected based on heart rate over a period of time, body temperature, blood temperature, blood pressure, interest level detection, and so forth. In other aspects, the biometric information provided by an eye-tracking sensor can be used to determine an interest level of the activity performed within the virtual application. For example, if the user's focal point is out-of-focus with respect to a pertinent object in the virtual application for a period of time, the user can be determined to be disengaged.

At block 506, if the computing system determines that the user activity information indicates fatigue of the user, the computing system can determine a corrective action to take based on an identified issue. For example, as described above with reference to FIG. 4, if the heart rate of the user exceeds a volume over a unit of time (e.g., 30 seconds), the computing system can determine that the user's cardiovascular system is fatigued and may need to recover before continuing. In another example, if the user activity information indicates that the user is disinterested, the computing system may determine a corrective action corresponding to the user's interest, such as altering the virtual application by requesting the user to perform a different event or function.

At block 508, if the computing system does not determine that the physiological information indicates fatigue of the user, the computing system may send at least one of the biometric information or the physiological information to the health monitoring service.

At block 510, the computing system determines whether the health monitoring service sends information to the computing system with information indicating fatigue. For example, the health monitoring system may send information including various information pertaining to an avatar of the user, and information pertaining to the physiological condition of the user. If the computing system receives information from the health monitoring service that indicates fatigue or other alert to be provided to the user, the computing system may perform block 506 and determine a corrective action to take as described above.

At block 512, if the computing system does not receive information indicating fatigue, the computing system may be configured to determine quality of motion information from the user activity information. For example, the computing system can compare expected motion to measured motion and determine a quality of motion. The movement quality can be a complex object that identifies a number of parameters, such as the path of movement, time of the movement, and so forth.

At block 514, the computing system can determine whether the quality of motion is sufficient to continue. If the quality of the motion is sufficient to continue, the computing system returns to block 502 and collects additional user activity information. If the quality of motion is not sufficient, the computing system may determine a corrective action to take based on an identified issue.

Figure 6B:
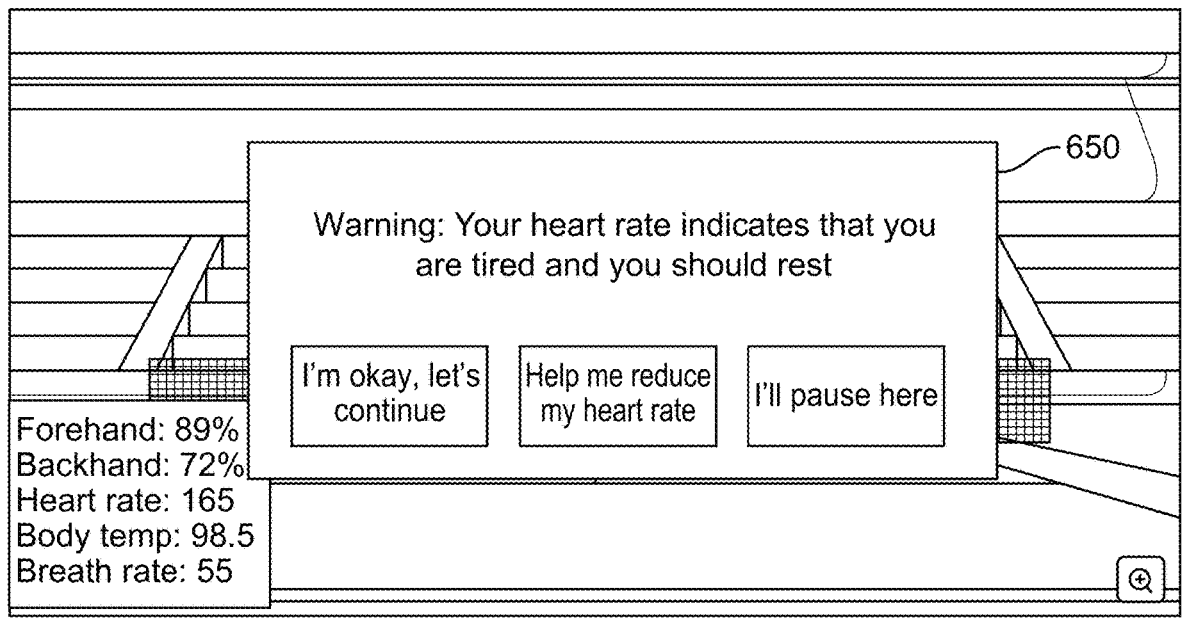

FIGS. 6A-6B are conceptual illustrations of a virtual application that can be executed by an XR device, in accordance with some aspects of the disclosure.

In particular, FIG. 6A illustrates a screenshot of a virtual application that is presented to a user of an XR device in accordance with some aspects of the disclosure. As illustrated in FIG. 6A, the virtual application comprises a tennis game that uses a VR controller 610 to control a virtual tennis racket and hit a tennis ball 620. In this illustrative example, the virtual application displays a motion 630 for the user to input using the VR controller 610 to hit the tennis ball 620. The virtual application also uses a heads up display (HUD) 640 that displays the user activity information, including the physiological information.

FIG. 6B illustrates a screenshot of a prompt that is displayed to the user of the XR device based on fatigue detection, in accordance with some aspects of the disclosure. In the example illustrated in FIG. 6B, the XR device detects that the user has become fatigued and displays a prompt 650 that requests input for the user that includes different recovery actions for the user. In this case, each recovery action may be associated with a particular reward to encourage a suitable recovery.

Figure 7A:
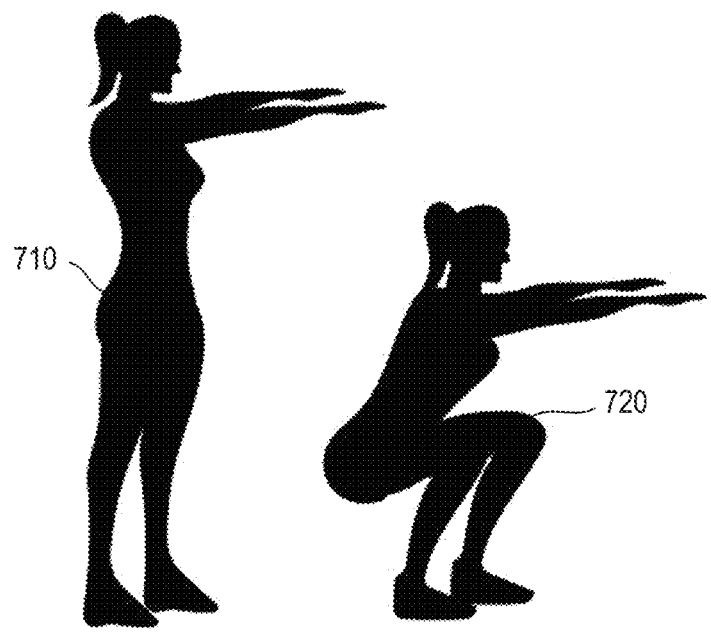
FIGS. 7A-7B are conceptual illustrations of various movements, in accordance with some aspects of the disclosure.
Figure 7B:
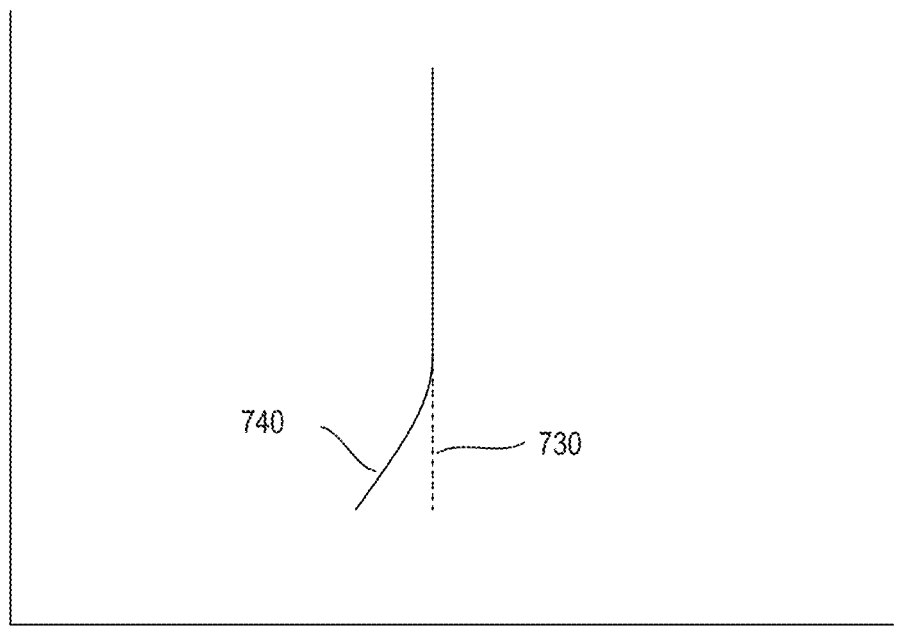

FIG. 7A-7B are conceptual illustrations of various movements that a user may perform in a virtual application, in accordance with some aspects of the disclosure. In one illustrative aspect, the virtual application is an exercise application that is configured to monitor movement. For example, the virtual application can be a customized training program that a user may follow to improve overall health. In some cases, the virtual application can be a fitness application that is customized to the user and monitors the user's movements.

FIG. 7A illustrates a motion that the virtual application may display to the user for the user to perform. In this case, the user starts in a standing position 710 and then lowers their body until they are in a compressed position 720. In this movement, the user should traverse a vertical path that has no lateral movement.

FIG. 7B illustrates a motion that is measured by the virtual application in accordance with aspects of the disclosure. In this case, the virtual application is expecting motion 730, which is a pure vertical line in the case of a squat. The measured motion 740 deviates from the expected motion 730. In some aspects, the measured motion 740 can occur because the user has lost interest and is not focusing on a spot in the virtual application to ensure a good head position. By shifting their focus, the user shifts their body forward by a small distance and thereby loads the weight of the squat onto their front foot, which causes the user to move forward at the bottom position of the squat. In this example, the virtual application can detect the lateral motion and inform the user to focus on a focal point provided by the virtual application to encourage a neutral head position, which can shift the load onto the heel of the user and prevent the lateral motion. The lateral motion at the bottom of the squat can cause injuries if the motion is repeated.

Figure 8:
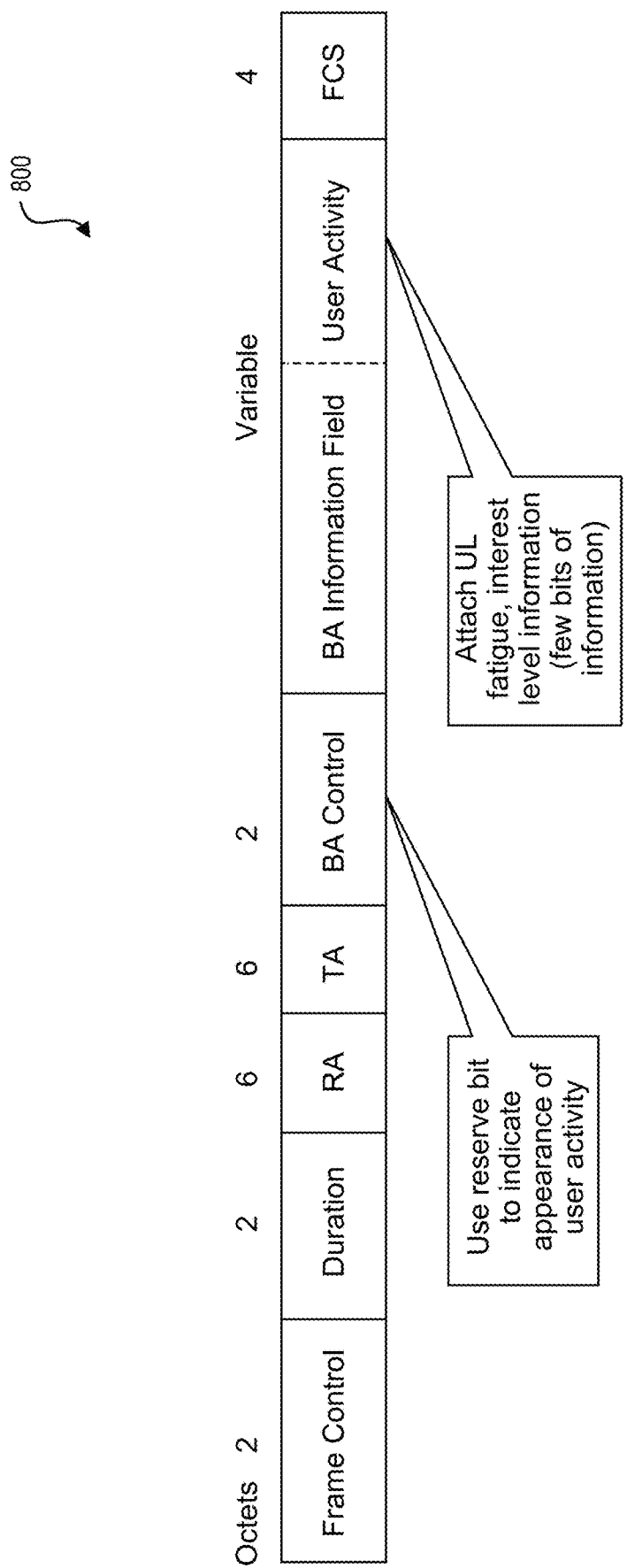
FIG. 8 is an illustration of a packet that is provided over a wireless communication network that includes biometric information for a monitoring service, in accordance with some aspects of the disclosure.

FIG. 8 is an illustration of an example packet 800 that can be provided over a wireless communication network that includes biometric information for a monitoring service, in accordance with some aspects of the disclosure. The packet 800 may include a block acknowledgement (ACK) packet and a block ACK (BA) control field. In one illustrative aspect, a bit can be reserved in the BA control field that indicates the packet 800 has space for additional content, such as information associated with user activity information of a user of an XR device (e.g., physiological information such as heart rate, blood pressure, temperature, etc.). A user activity field can include the user activity information.

Figure 9:
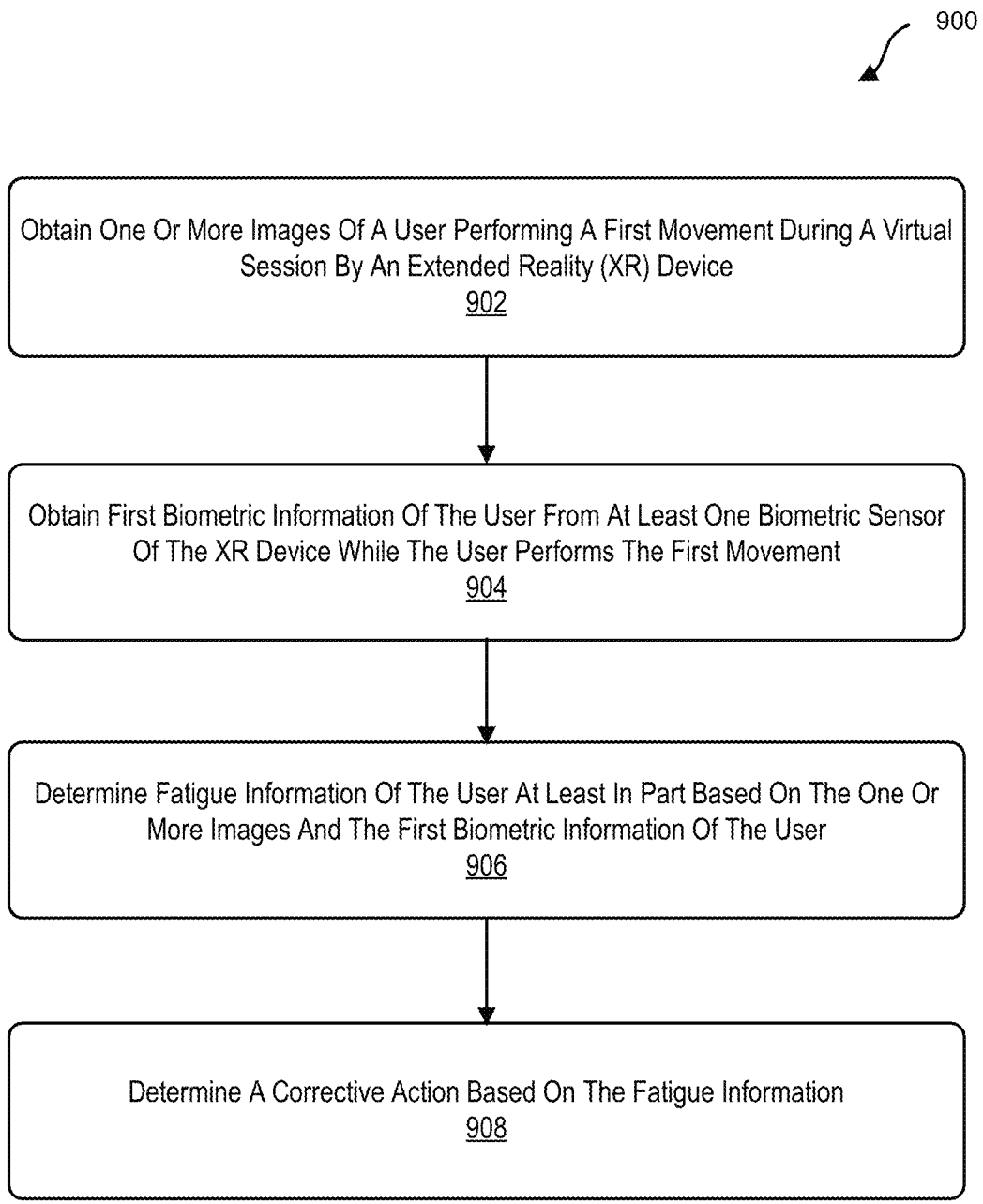
FIG. 9 is a flowchart illustrating an example of a method for processing touch input with an adaptive touch sensor, in accordance with certain aspects of the present disclosure.

FIG. 9 is a flowchart illustrating an example of a method 900 for monitoring activity of a person, in accordance with certain aspects of the present disclosure. The methods 500 and 900 can be performed by an XR device or by a computing device (or a component of the computing device) connected to an XR device, such as a mobile wireless communication device, a smart speaker, a camera, an XR device, a wireless-enabled vehicle, or another computing device. In one illustrative example, a computing system 1000 can be configured to perform all or part of the method 500.

At block 902, the computing system (e.g., the computing system 1000) is configured to obtain one or more images of a user performing a first movement during a usage instance of an XR device. In some aspects, the usage instance is a user executing an application to cause content to be rendered to the XR device for the user to consume for various interactions.

At block 904, the computing system (e.g., the computing system 1000) is configured to obtain first biometric information of the user from at least one first biometric sensor of the XR device while the user performs the first movement. The first biometric information may include a various information such as at least one of blood pressure, pulse rate, blood-oxygen levels, or respiration rate.

In some aspects, the at least one first biometric sensor comprises at least one of a PPG sensor or a first eye tracking sensor configured to measure characteristics associated with an eye of the user. In some other aspects, the at least one first biometric sensor comprises a RF sensor configured to measure at least a portion of the first biometric information based on one or more wireless signals. For example, an RF sensor is a microwave transceiver that transmits and receives millimeter wavelength signal (e.g., 60 GHz) that can measure chest position to determine respiratory rate.

In some aspects, the at least one first biometric sensor may include an eye tracking sensor. In this case, to obtain the first biometric information, the computing system can measure, based on information obtained using the eye tracking sensor, a plurality of characteristics associated with at least one eye of the user. Non-limiting examples of a plurality of characteristics associated with at least one eye of the user include comprise at least one of a shape of the at least one eye, a pupil measurement of the at least one eye, a blinking rate of the at least one eye, oculomotor-based metrics of the at least one eye, gaze allocation of the at least one eye, one or more eye movement directions of the at least one eye, or a saliency model associated with the at least one eye. In some cases, the computing system may determine the fatigue information based on a respective weight associated with each characteristic of the plurality of characteristics associated with the at least one eye of the user.

At block 906, the computing system (e.g., the computing system 1000) is configured to determine fatigue information of the user at least in part based on the one or more images and the first biometric information of the user. In other cases, the fatigue information can relate to aspects of the virtual session, such as a movement quality. For example, the computing system may determine a movement quality associated with the first movement based on motion data from at least one motion sensor and determine the fatigue information further based on the movement quality. The movement quality can be a metric of an expected motion versus measured motion.

In some aspects, the computing system may be configured to obtain second biometric information from an external device, and the external device can include at least one second biometric sensor. In some aspects, the external device is held by or attached to the user and includes at least one PPG sensor. For example, the external device may be a wireless or a wired controller that is held by the user to perform motion and other user input. In another example, the external device is connected to the XR device to form an electrical loop configured for an EKG measurement. In this case, the computing system further determines the fatigue information based on the second biometric information determine fatigue information.

In some other aspects, to determine the fatigue information of the user, the computing system may use focal information of an eye of the user. For example, the computing system may determine that a focal point of the user is out-of-focus based on a focal point of the one or more images and, based on the focal point of the user being out-of-focus, perform an intervening action for at least a duration for which the focal point of the user is out-of-focus. The intervening action can cause a prompt that results in the user changing the activity. For example, the computing system may display an alert based on the duration being greater than a first time, prompt the user to consent to continue the usage instance based on the duration being greater than a second time, or perform the action based on the duration being greater than a third time, wherein the action comprises pausing the usage instance.

At block 908, the computing system (e.g., the computing system 1000) is configured to determine an action based on the fatigue information. In some aspects, the action comprises a second movement that is different from the first movement. For example, the action comprises a recovery action, and the recovery action enables the user's body to recover (e.g., to reduce the user's heart rate). In some cases, the action comprises pausing the usage instance based on the fatigue information. Other types of actions are possible, such as scaling the difficulty of the movement.

In some cases, the computing system may obtain, based on user input from the user, a request to continue the usage instance for the user after the usage instance is paused. The computing system may be configured to control the usage instance. For example, the computing system may obtain, based on the request, at least one of second biometric information from the at least one first biometric sensor or one or more additional images of the user and determine, based on at least one of the second biometric information or the one or more additional images, whether to continue the usage instance for the user. In this case, the computing system controls whether the user can re-engage with the usage instance based on measured biometric information.

In some aspects, the computing system may be configured to obtain visual feedback information for application to an avatar representing the user in the usage instance. For example, the visual feedback information is associated with the fatigue information and may be displayed to the suer. In this case, the visual feedback information identifies at least one physical characteristic associated with the fatigue information.

In some aspects, at least a portion of the first biometric information is provided to a health monitoring service. For example, when the computing system determines the fatigue information, the computing system may receive at least a portion of the fatigue information from the health monitoring service. The computing system can use the fatigue information from the health monitoring service to proactively monitor the user for adverse issues, such as atrial fibrillation.

In some examples, the processes described herein (e.g., methods 500 and 900, and/or other processes described herein) may be performed by a computing device or apparatus. In one example, the methods 500 and 900 can be performed by a computing device including a touch screen having a computing architecture of the computing system 1000 shown in FIG. 10.

The computing device can include any suitable device, such as a mobile device (e.g., a mobile phone), a desktop computing device, a tablet computing device, a wearable device (e.g., a VR headset, an AR headset, AR glasses, a network-connected watch or smartwatch, or other wearable device), a server computer, an autonomous vehicle or computing device of an autonomous vehicle, a robotic device, a television, and/or any other computing device with the resource capabilities to perform the methods described herein, including the methods 500 and 900. In some cases, the computing device or apparatus may include various components, such as one or more input devices, one or more output devices, one or more processors, one or more microprocessors, one or more microcomputers, one or more cameras, one or more sensors, and/or other component(s) that are configured to carry out the steps of methods described herein. In some examples, the computing device may include a display, a network interface configured to communicate and/or receive the data, any combination thereof, and/or other component(s). The network interface may be configured to communicate and/or receive IP-based data or other type of data.

The components of the computing device can be implemented in circuitry. For example, the components can include and/or can be implemented using electronic circuits or other electronic hardware, which can include one or more programmable electronic circuits (e.g., microprocessors, GPUs, DSPs, CPUs, and/or other suitable electronic circuits), and/or can include and/or be implemented using computer software, firmware, or any combination thereof, to perform the various operations described herein.

The methods 500 and 900 are illustrated as logical flow diagrams, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the methods.

The methods 500 and 900 and/or other method or process described herein may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable or machine-readable storage medium, for example, in the form of a computer program comprising a plurality of instructions executable by one or more processors. The computer-readable or machine-readable storage medium may be non-transitory.

FIG. 10 is a diagram illustrating an example of a system for implementing certain aspects of the present technology. In particular, FIG. 10 illustrates an example of computing system 1000, which can be for example any computing device making up internal computing system, a remote computing system, a camera, or any component thereof in which the components of the system are in communication with each other using connection 1005. Connection 1005 can be a physical connection using a bus, or a direct connection into processor 1010, such as in a chipset architecture. Connection 1005 can also be a virtual connection, networked connection, or logical connection.

In some aspects, computing system 1000 is a distributed system in which the functions described in this disclosure can be distributed within a datacenter, multiple data centers, a peer network, etc. In some aspects, one or more of the described system components represents many such components each performing some or all of the function for which the component is described. In some aspects, the components can be physical or virtual devices.

Example computing system 1000 includes at least one processing unit (CPU or processor) 1010 and connection 1005 that couples various system components including system memory 1015, such as ROM 1020 and RAM 1025 to processor 1010. Computing system 1000 can include a cache 1012 of high-speed memory connected directly with, in close proximity to, or integrated as part of processor 1010.

Processor 1010 can include any general purpose processor and a hardware service or software service, such as services 1032, 1034, and 1036 stored in storage device 1030, configured to control processor 1010 as well as a special-purpose processor where software instructions are incorporated into the actual processor design. Processor 1010 may essentially be a completely self-contained computing system, containing multiple cores or processors, a bus, memory controller, cache, etc. A multi-core processor may be symmetric or asymmetric.

To enable user interaction, computing system 1000 includes an input device 1045, which can represent any number of input mechanisms, such as a microphone for speech, a touch-sensitive screen for gesture or graphical input, keyboard, mouse, motion input, speech, etc. Computing system 1000 can also include output device 1035, which can be one or more of a number of output mechanisms. In some instances, multimodal systems can enable a user to provide multiple types of input/output to communicate with computing system 1000. Computing system 1000 can include communications interface 1040, which can generally govern and manage the user input and system output. The communication interface may perform or facilitate receipt and/or transmission wired or wireless communications using wired and/or wireless transceivers, including those making use of an audio jack/plug, a microphone jack/plug, a universal serial bus (USB) port/plug, an Apple® Lightning® port/plug, an Ethernet port/plug, a fiber optic port/plug, a proprietary wired port/plug, a Bluetooth® wireless signal transfer, a BLE wireless signal transfer, an IBEACON® wireless signal transfer, an RFID wireless signal transfer, near-field communications (NFC) wireless signal transfer, dedicated short range communication (DSRC) wireless signal transfer, 802.11 WiFi wireless signal transfer, WLAN signal transfer, Visible Light Communication (VLC), Worldwide Interoperability for Microwave Access (WiMAX), IR communication wireless signal transfer, Public Switched Telephone Network (PSTN) signal transfer, Integrated Services Digital Network (ISDN) signal transfer, 3G/4G/5G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. The communications interface 1040 may also include one or more Global Navigation Satellite System (GNSS) receivers or transceivers that are used to determine a location of the computing system 1000 based on receipt of one or more signals from one or more satellites associated with one or more GNSS systems. GNSS systems include, but are not limited to, the US-based GPS, the Russia-based Global Navigation Satellite System (GLONASS), the China-based BeiDou Navigation Satellite System (BDS), and the Europe-based Galileo GNSS. There is no restriction on operating on any particular hardware arrangement, and therefore the basic features here may easily be substituted for improved hardware or firmware arrangements as they are developed.

Storage device 1030 can be a non-volatile and/or non-transitory and/or computer-readable memory device and can be a hard disk or other types of computer readable media which can store data that are accessible by a computer, such as magnetic cassettes, flash memory cards, solid state memory devices, digital versatile disks, cartridges, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, RAM, static RAM (SRAM), dynamic RAM (DRAM), ROM, programmable read-only memory (PROM), erasable programmable read-only memory (EPROM), electrically erasable programmable read-only memory (EEPROM), flash EPROM (FLASHEPROM), cache memory (L1/L2/L3/L4/L5/L #), resistive random-access memory (RRAM/ReRAM), phase change memory (PCM), spin transfer torque RAM (STT-RAM), another memory chip or cartridge, and/or a combination thereof.

The storage device 1030 can include software services, servers, services, etc., that when the code that defines such software is executed by the processor 1010, it causes the system to perform a function. In some aspects, a hardware service that performs a particular function can include the software component stored in a computer-readable medium in connection with the necessary hardware components, such as processor 1010, connection 1005, output device 1035, etc., to carry out the function. The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as CD or DVD, flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

In some cases, the computing device or apparatus may include various components, such as one or more input devices, one or more output devices, one or more processors, one or more microprocessors, one or more microcomputers, one or more cameras, one or more sensors, and/or other component(s) that are configured to carry out the steps of processes described herein. In some examples, the computing device may include a display, one or more network interfaces configured to communicate and/or receive the data, any combination thereof, and/or other component(s). The one or more network interfaces can be configured to communicate and/or receive wired and/or wireless data, including data according to the 3G, 4G, 5G, and/or other cellular standard, data according to the Wi-Fi (802.11x) standards, data according to the Bluetooth™ standard, data according to the IP standard, and/or other types of data.

The components of the computing device can be implemented in circuitry. For example, the components can include and/or can be implemented using electronic circuits or other electronic hardware, which can include one or more programmable electronic circuits (e.g., microprocessors, GPUs, DSPs, CPUs, and/or other suitable electronic circuits), and/or can include and/or be implemented using computer software, firmware, or any combination thereof, to perform the various operations described herein.

In some aspects the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Specific details are provided in the description above to provide a thorough understanding of the aspects and examples provided herein. However, it will be understood by one of ordinary skill in the art that the aspects may be practiced without these specific details. For clarity of explanation, in some instances the present technology may be presented as including individual functional blocks including functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the aspects in unnecessary detail. In other instances, well-known circuits, processes, algorithms, structures, and techniques may be shown without unnecessary detail in order to avoid obscuring the aspects.

Individual aspects may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed but may have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc. Examples of computer-readable media that may be used to store instructions, information used, and/or information created during methods according to described examples include magnetic or optical disks, flash memory, USB devices provided with non-volatile memory, networked storage devices, and so on.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices, or other small form factor personal computers, personal digital assistants, rackmount devices, standalone devices, and so on. The functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific aspects thereof, but those skilled in the art will recognize that the application is not limited thereto. Thus, while illustrative aspects of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, aspects can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate aspects, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language reciting "at least one of" a set and/or "one or more" of a set indicates that one member of the set or multiple members of the set (in any combination) satisfy the claim. For example, claim language reciting "at least one of A and B" or "at least one of A or B" means A, B, or A and B. In another example, claim language reciting "at least one of A, B, and C" or "at least one of A, B, or C" means A, B, C, or A and B, or A and C, or B and C, or A and B and C. The language "at least one of" a set and/or "one or more" of a set does not limit the set to the items listed in the set. For example, claim language reciting "at least one of A and B" or "at least one of A or B" can mean A, B, or A and B, and can additionally include items not listed in the set of A and B.

The various illustrative logical blocks, modules, circuits, and algorithm steps described in connection with the aspects disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as RAM such as synchronous dynamic random access memory (SDRAM), ROM, nonvolatile random access memory (NVRAM), EEPROM, flash memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more DSPs, general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein.

Illustrative aspects of the disclosure include:

Aspect 1. A method for monitoring activity of a person, comprising: obtaining one or more images of a user performing a first movement during a usage instance of an extended reality (XR) device; obtaining first biometric information of the user from at least one first biometric sensor of the XR device while the user performs the first movement; determining fatigue information of the user at least in part based on the one or more images and the first biometric information of the user; and determining an action based on the fatigue information.

Aspect 2. The method of Aspect 1, wherein the at least one first biometric sensor comprises at least one of a photoplethysmography (PPG) sensor or a first eye tracking sensor configured to measure characteristics associated with an eye of the user.

Aspect 3. The method of any of Aspects 1 to 2, wherein the at least one first biometric sensor comprises a radio frequency (RF) sensor configured to measure at least a portion of the first biometric information based on one or more wireless signals.

Aspect 4. The method of any of Aspects 1 to 3, further comprising: obtaining second biometric information from an external device including at least one second biometric sensor; and determining the fatigue information further based on the second biometric information.

Aspect 5. The method of Aspect 4, wherein the external device is held by or attached to the user and includes at least one PPG sensor.

Aspect 6. The method of any of Aspects 4 to 5, wherein the external device is connected to the XR device to form an electrical loop configured for an electrocardiogram (EKG) measurement.

Aspect 7. The method of any of Aspects 1 to 6, wherein the action comprises a second movement that is different from the first movement.

Aspect 8. The method of any of Aspects 1 to 7, wherein the action comprises a recovery action.

Aspect 9. The method of any of Aspects 1 to 8, wherein the action comprises pausing the usage instance based on the fatigue information.

Aspect 10. The method of Aspect 9, further comprising: obtaining, based on user input from the user, a request to continue the usage instance for the user after the usage instance is paused; obtaining, based on the request, at least one of second biometric information from the at least one first biometric sensor or one or more additional images of the user; and determining, based on at least one of the second biometric information or the one or more additional images, whether to continue the usage instance for the user.

Aspect 11. The method of any of Aspects 1 to 10, further comprising: determining a movement quality associated with the first movement based on motion data from at least one motion sensor; and determining the fatigue information further based on the movement quality.

Aspect 12. The method of any of Aspects 1 to 11, wherein the first biometric information comprises at least one of blood pressure, pulse rate, blood-oxygen levels, or respiration rate.

Aspect 13. The method of any of Aspects 1 to 12, wherein the at least one first biometric sensor includes an eye tracking sensor, and wherein obtaining the first biometric information comprises: measuring, based on information obtained using the eye tracking sensor, a plurality of characteristics associated with at least one eye of the user.

Aspect 14. The method of Aspect 13, further comprising: determining the fatigue information based on a respective weight associated with each characteristic of the plurality of characteristics associated with the at least one eye of the user, wherein the plurality of characteristics comprise at least one of a shape of the at least one eye, a pupil measurement of the at least one eye, a blinking rate of the at least one eye, oculomotor-based metrics of the at least one eye, gaze allocation of the at least one eye, one or more eye movement directions of the at least one eye, or a saliency model associated with the at least one eye.

Aspect 15. The method of any of Aspects 1 to 14, wherein determining the fatigue information of the user comprises: determining that a focal point of the user is out-of-focus based on a focal point of the one or more images; and based on the focal point of the user being out-of-focus, performing an intervening action for at least a duration for which the focal point of the user is out-of-focus.

Aspect 16. The method of Aspect 15, wherein the intervening action comprises at least one of: displaying an alert based on the duration being greater than a first time; prompting the user to consent to continue the usage instance based on the duration being greater than a second time; or performing the action based on the duration being greater than a third time, wherein the action comprises pausing the usage instance.

Aspect 17. The method of any of Aspects 1 to 16, further comprising: obtaining visual feedback information for application to an avatar representing the user in the usage instance, wherein the visual feedback information is associated with the fatigue information.

Aspect 18. The method of Aspect 17, wherein the visual feedback information identifies at least physical characteristic associated with the fatigue information.

Aspect 19. The method of any of Aspects 1 to 18, wherein at least a portion of the first biometric information is provided to a health monitoring service.

Aspect 20. The method of Aspect 19, wherein determining the fatigue information comprises receiving at least a portion of the fatigue information from the health monitoring service.

Aspect 21. An apparatus for monitoring activity of a person. The apparatus includes at least one memory and at least one processor coupled to the at least one memory. The at least one processor is configured to: obtain one or more images of a user performing a first movement during a usage instance of an XR device; obtain first biometric information of the user from at least one first biometric sensor of the XR device while the user performs the first movement; determine fatigue information of the user at least in part based on the one or more images and the first biometric information of the user; and determine an action based on the fatigue information.

Aspect 22. The apparatus of Aspect 21, wherein the at least one first biometric sensor comprises at least one of a PPG sensor or a first eye tracking sensor configured to measure characteristics associated with an eye of the user.

Aspect 23. The apparatus of any of Aspects 21 to 22, wherein the at least one first biometric sensor comprises a RF sensor configured to measure at least a portion of the first biometric information based on one or more wireless signals.

Aspect 24. The apparatus of any of Aspects 21 to 23, wherein the at least one processor is configured to: obtain second biometric information from an external device including at least one second biometric sensor; and determine the fatigue information further based on the second biometric information.

Aspect 25. The apparatus of Aspect 24, wherein the external device is held by or attached to the user and includes at least one PPG sensor.

Aspect 26. The apparatus of any of Aspects 24 to 25, wherein the external device is connected to the XR device to form an electrical loop configured for an electrocardiogram (EKG) measurement.

Aspect 27. The apparatus of any of Aspects 21 to 26, wherein the action comprises a second movement that is different from the first movement.

Aspect 28. The apparatus of any of Aspects 21 to 27, wherein the action comprises a recovery action.

Aspect 29. The apparatus of any of Aspects 21 to 28, wherein the action comprises pausing the usage instance based on the fatigue information.

Aspect 30. The apparatus of Aspect 29, wherein the at least one processor is configured to obtain, based on user input from the user, a request to continue the usage instance for the user after the usage instance is paused, obtain, based on the request, at least one of second biometric information from the at least one first biometric sensor or one or more additional images of the user, or determine, based on at least one of the second biometric information or the one or more additional images, whether to continue the usage instance for the user.

Aspect 31. The apparatus of any of Aspects 21 to 30, wherein the at least one processor is configured to: determine a movement quality associated with the first movement based on motion data from at least one motion sensor; and determine the fatigue information further based on the movement quality.

Aspect 32. The apparatus of any of Aspects 21 to 31, wherein the first biometric information comprises at least one of blood pressure, pulse rate, blood-oxygen levels, or respiration rate.

Aspect 33. The apparatus of any of Aspects 21 to 32, wherein the at least one first biometric sensor includes an eye tracking sensor, and wherein the at least one processor is configured to: measure, based on information obtained using the eye tracking sensor, a plurality of characteristics associated with at least one eye of the user.

Aspect 34. The apparatus of Aspect 33, wherein the at least one processor is configured to: determine the fatigue information based on a respective weight associated with each characteristic of the plurality of characteristics associated with the at least one eye of the user, wherein the plurality of characteristics comprise at least one of a shape of the at least one eye, a pupil measurement of the at least one eye, a blinking rate of the at least one eye, oculomotor-based metrics of the at least one eye, gaze allocation of the at least one eye, one or more eye movement directions of the at least one eye, or a saliency model associated with the at least one eye.

Aspect 35. The apparatus of any of Aspects 21 to 34, wherein the at least one processor is configured to determine that a focal point of the user is out-of-focus based on a focal point of the one or more images, and based on the focal point of the user being out-of-focus, perform an intervening action for at least a duration for which the focal point of the user is out-of-focus.

Aspect 36. The apparatus of Aspect 35, wherein, based on the intervening action, the at least one processor is configured to at least one of: display an alert based on the duration being greater than a first time; prompt the user to consent to continue the usage instance based on the duration being greater than a second time; or perform the action based on the duration being greater than a third time, wherein the action comprises pausing the usage instance.

Aspect 37. The apparatus of any of Aspects 21 to 36, wherein the at least one processor is configured to: obtain visual feedback information for application to an avatar representing the user in the usage instance, wherein the visual feedback information is associated with the fatigue information.

Aspect 38. The apparatus of Aspect 37, wherein the visual feedback information identifies at least physical characteristic associated with the fatigue information.

Aspect 39. The apparatus of any of Aspects 21 to 38, wherein at least a portion of the first biometric information is provided to a health monitoring service.

Aspect 40. The apparatus of Aspect 39, wherein, to determine the fatigue information, the at least one processor is configured to receive at least a portion of the fatigue information from the health monitoring service.

Aspect 41: A non-transitory computer-readable medium comprising instructions which, when executed by one or more processors, cause the one or more processors to perform operations according to any of Aspects 1 to 20.

Aspect 42: An apparatus comprising means for performing operations according to any of Aspects 1 to 20.

What is claimed is:

1. A method for monitoring activity of a person, comprising:
   obtaining one or more images of a user performing a first movement during a usage instance of an extended reality (XR) device;
   obtaining first biometric information of the user from at least one first biometric sensor of the XR device while the user performs the first movement;
   obtaining second biometric information of the user generated based on an electrical loop from a second biometric sensor of an external device to the XR device, wherein a first portion of the electrical loop comprises a wire connected from the external device to the XR device and a second portion of the electrical loop is formed between an electrode of the external device and an electrode of the XR device;
   determining fatigue information of the user at least in part based on the one or more images, the first biometric information of the user, and the second biometric information of the user;
   determining an action based on the fatigue information, wherein the action comprises pausing the usage instance based on the fatigue information;
   obtaining, based on user input from the user, a request to continue the usage instance for the user after the usage instance is paused;
   obtaining, based on the request, at least one of third biometric information from the at least one first biometric sensor or one or more additional images of the user; and
   determining, based on at least one of the third biometric information or the one or more additional images, whether to continue the usage instance for the user.

2. The method of claim 1, wherein the at least one first biometric sensor comprises at least one of a photoplethysmography (PPG) sensor or a first eye tracking sensor configured to measure characteristics associated with an eye of the user.

3. The method of claim 1, wherein the at least one first biometric sensor comprises a radio frequency (RF) sensor configured to measure at least a portion of the first biometric information based on one or more wireless signals.

4. The method of claim 1, wherein the external device is held by the user and includes at least one PPG sensor.

5. The method of claim 1, wherein the external device is connected to the XR device to form the electrical loop for an electrocardiogram (EKG) measurement.

6. The method of claim 1, wherein the action comprises a second movement that is different from the first movement.

7. The method of claim 1, wherein the action comprises a recovery action.

8. The method of claim 1, further comprising:
   determining a movement quality associated with the first movement based on motion data from at least one motion sensor; and
   determining the fatigue information further based on the movement quality.

9. The method of claim 1, wherein the first biometric information comprises at least one of blood pressure, pulse rate, blood-oxygen levels, or respiration rate.

10. The method of claim 1, wherein the at least one first biometric sensor includes an eye tracking sensor, and wherein obtaining the first biometric information comprises:
    measuring, based on information obtained using the eye tracking sensor, a plurality of characteristics associated with at least one eye of the user.

11. The method of claim 10, further comprising:
    determining the fatigue information based on a respective weight associated with each characteristic of the plurality of characteristics associated with the at least one eye of the user, wherein the plurality of characteristics comprise at least one of a shape of the at least one eye, a pupil measurement of the at least one eye, a blinking rate of the at least one eye, oculomotor-based metrics of the at least one eye, gaze allocation of the at least one eye, one or more eye movement directions of the at least one eye, or a saliency model associated with the at least one eye.

12. The method of claim 1, wherein determining the fatigue information of the user comprises:
    determining that a focal point of the user is out-of-focus based on a focal point of the one or more images; and
    based on the focal point of the user being out-of-focus, performing an intervening action for at least a duration for which the focal point of the user is out-of-focus.

13. The method of claim 12, wherein the intervening action comprises at least one of:
    displaying an alert based on the duration being greater than a first time;
    prompting the user to consent to continue the usage instance based on the duration being greater than a second time; or
    performing the action based on the duration being greater than a third time, wherein the action comprises pausing the usage instance.

14. The method of claim 1, further comprising:
    obtaining visual feedback information for application to an avatar representing the user in the usage instance, wherein the visual feedback information is associated with the fatigue information.

15. The method of claim 14, wherein the visual feedback information identifies at least one physical characteristic associated with the fatigue information.

16. The method of claim 1, wherein at least a portion of the first biometric information is provided to a health monitoring service.

17. The method of claim 16, wherein determining the fatigue information comprises receiving at least a portion of the fatigue information from the health monitoring service.

18. An apparatus for monitoring activity of a person, comprising:
    at least one memory; and
    at least one processor coupled to the at least one memory and configured to:

obtain one or more images of a user performing a first movement during a usage instance of an extended reality (XR) device;
obtain first biometric information of the user from at least one first biometric sensor of the XR device while the user performs the first movement;
obtain second biometric information of the user generated based on an electrical loop from a second biometric sensor of external device to the XR device, wherein a first portion of the electrical loop comprises a wire connected from the external device to the XR device and a second portion of the electrical loop is formed between an electrode of the external device and an electrode of the XR device;
determine fatigue information of the user at least in part based on the one or more images, the first biometric information of the user, and the second biometric information of the user;
determine an action based on the fatigue information, wherein the action comprises pausing the usage instance based on the fatigue information;
obtain, based on user input from the user, a request to continue the usage instance for the user after the usage instance is paused;
obtain, based on the request, at least one of third biometric information from the at least one first biometric sensor or one or more additional images of the user; and
determine, based on at least one of the third biometric information or the one or more additional images, whether to continue the usage instance for the user.

19. The apparatus of claim 18, wherein the at least one first biometric sensor comprises at least one of a photoplethysmography (PPG) sensor or a first eye tracking sensor configured to measure characteristics associated with an eye of the user.

20. The apparatus of claim 18, wherein the at least one first biometric sensor comprises a radio frequency (RF) sensor configured to measure at least a portion of the first biometric information based on one or more wireless signals.

21. The apparatus of claim 18, wherein the external device is held by the user and includes at least one PPG sensor.

22. The apparatus of claim 18, wherein the external device is connected to the XR device to form the electrical loop for an electrocardiogram (EKG) measurement.

23. The apparatus of claim 18, wherein the action comprises a second movement that is different from the first movement.

24. The apparatus of claim 18, wherein the action comprises a recovery action.

25. The apparatus of claim 18, wherein the at least one processor is configured to:
determine a movement quality associated with the first movement based on motion data from at least one motion sensor; and
determine the fatigue information further based on the movement quality.

26. The apparatus of claim 18, wherein the first biometric information comprises at least one of blood pressure, pulse rate, blood-oxygen levels, or respiration rate.

27. The apparatus of claim 18, wherein the at least one processor is configured to:
obtain motion data associated with movement of the external device, wherein a motion sensor of the external device detects the movement,
wherein the second biometric information of the user is obtained concurrently with the motion data, and
wherein the motion data is provided to the XR device for interacting with the usage instance of the XR device.

28. The apparatus of claim 18, wherein the at least one first biometric sensor includes an eye tracking sensor, and wherein the at least one processor is configured to:
measure, based on information obtained using the eye tracking sensor, a plurality of characteristics associated with at least one eye of the user.

29. The apparatus of claim 28, wherein the at least one processor is configured to:
determine the fatigue information based on a respective weight associated with each characteristic of the plurality of characteristics associated with the at least one eye of the user, wherein the plurality of characteristics comprise at least one of a shape of the at least one eye, a pupil measurement of the at least one eye, a blinking rate of the at least one eye, oculomotor-based metrics of the at least one eye, gaze allocation of the at least one eye, one or more eye movement directions of the at least one eye, or a saliency model associated with the at least one eye.

30. The apparatus of claim 18, wherein the at least one processor is configured to:
determine that a focal point of the user is out-of-focus based on a focal point of the one or more images; and
based on the focal point of the user being out-of-focus, perform an intervening action for at least a duration for which the focal point of the user is out-of-focus.

31. The apparatus of claim 30, wherein, based on the intervening action, the at least one processor is configured to at least one of:
display an alert based on the duration being greater than a first time;
prompt the user to consent to continue the usage instance based on the duration being greater than a second time; or
perform the action based on the duration being greater than a third time, wherein the action comprises pausing the usage instance.

32. The apparatus of claim 18, wherein the at least one processor is configured to:
obtain visual feedback information for application to an avatar representing the user in the usage instance, wherein the visual feedback information is associated with the fatigue information.

33. The apparatus of claim 32, wherein the visual feedback information identifies at least physical characteristic associated with the fatigue information.

34. The apparatus of claim 18, wherein at least a portion of the first biometric information is provided to a health monitoring service.

35. The apparatus of claim 34, wherein, to determine the fatigue information, the at least one processor is configured to receive at least a portion of the fatigue information from the health monitoring service.

36. A method for monitoring activity of a person, comprising:
obtaining one or more images of a user performing a first movement during a usage instance of an extended reality (XR) device;
obtaining first biometric information of the user from at least one first biometric sensor of the XR device while the user performs the first movement;
obtaining second biometric information of the user generated based on an electrical loop from a second biometric sensor of an external device to the XR device, wherein a first portion of the electrical loop comprises a wire connected from the external device to the XR device and a second portion of the electrical loop is formed between an electrode of the external device and an electrode of the XR device;

obtaining motion data associated with movement of the external device for input, wherein a motion sensor of the external device detects the movement;

determining fatigue information of the user at least in part based on the one or more images, the first biometric information of the user, and the second biometric information of the user; and determining an action based on the fatigue information, wherein the second biometric information of the user is obtained concurrently with the motion data, and wherein the motion data is provided to the XR device for interacting with the usage instance of the XR device.

\* \* \* \* \*